(12) United States Patent
Lanar et al.

(10) Patent No.: US 7,029,685 B2
(45) Date of Patent: Apr. 18, 2006

(54) PLASMODIUM FALCIPARUM AMA-1 PROTEIN AND USES THEREOF

(75) Inventors: David E. Lanar, Takoma Park, MD (US); Sheetij Dutta, Silver Spring, MD (US); Lisa A. Ware, Silver Spring, MD (US); Lalitha P. V. Nair, New Delhi (IN)

(73) Assignee: The United States of America as represented by the Secretary of the Army, Washington, DC (US)

( * ) Notice: Subject to any disclaimer, the term of this patent is extended or adjusted under 35 U.S.C. 154(b) by 106 days.

(21) Appl. No.: 10/271,145

(22) Filed: Oct. 15, 2002

(65) Prior Publication Data

US 2003/0138450 A1    Jul. 24, 2003

Related U.S. Application Data

(63) Continuation-in-part of application No. 10/105,717, filed on Mar. 25, 2002.

(60) Provisional application No. 60/278,616, filed on Mar. 26, 2001.

(51) Int. Cl.
*A61K 39/15* (2006.01)
*A61K 39/00* (2006.01)
*C07H 21/04* (2006.01)
*C12N 15/63* (2006.01)
*C12N 15/09* (2006.01)

(52) U.S. Cl. ............................ 424/272.1; 424/268.1; 424/265.1; 424/199.1; 424/190.1; 424/185.1; 530/350; 536/23.7; 435/320.1; 435/172.3; 435/69.3

(58) Field of Classification Search ............ 424/272.1, 424/268.1, 265.1, 199.1, 190.1, 185.1; 435/320.1, 435/172.3, 69.3; 530/350; 536/23.7
See application file for complete search history.

(56) References Cited

U.S. PATENT DOCUMENTS 5,766,597 A    6/1998   Paoletti et al.

*Primary Examiner*—Lynette R. F. Smith
*Assistant Examiner*—Padma Baskar
(74) *Attorney, Agent, or Firm*—Elizabeth Arwine

(57) ABSTRACT

In this application is described the expression and purification of a recombinant *Plasmodium falciparum* (3D7) AMA-1 ectodomain. The method of the present invention produces a highly purified protein which retains folding and disulfide bridging of the native molecule. The recombinant AMA-1 is useful as a diagnostic reagent, for use in antibody production, and as a protein for use alone, or as part of, a vaccine to prevent malaria.

20 Claims, 9 Drawing Sheets

PLASMODIUM FALCIPARUM AMA-1 PROTEIN AND USES THEREOF

This is a countinutation-in-part application which claims the benefit of priority under 35 U.S.C. §120 from U.S. application Ser. No. 10/105,717 filed on Mar. 25, 2002, still pending which claims priority under 35 U.S.C. §119(e) from U.S. application Ser. No. 60/278,616 filed on Mar. 26, 2001, now abandoned.

FIELD OF THE INVENTION

The present invention relates to a purified *Plasmodium falciparum* protein. More particularly, this invention is directed to a composition comprising a portion of the *Plasmodium falciparum* AMA-1 protein for use as a vaccine.

INTRODUCTION

*Plasmodium falciparum* causes more than three million deaths each year, mostly among children below the age of five (World Health Organization Tropical Disease Research, 1997, TDR Twelfth Program Report, p. 57–76). The spread of multi-drug resistant strains of the parasite has underlined an urgent need for a malaria vaccine. Evidence exists both from animal models and human studies that antibodies to erythrocytic and exo-erythrocytic parasite antigens can induce protection. Apical membrane antigen-1 (AMA1) is one of the most promising erythrocytic stage vaccine targets under investigation. Present on the extra-cellular merozoite stage of the parasite, AMA1, is amenable to host immune intervention during the process of invasion. Indeed, immunization in animal models with affinity purified or recombinant forms of AMA1 along with adjuvants permissible for human-use, can induce a protective response against homologous parasite challenge in vivo (Deans, et al., 1988, Parasite Immunol. 10, 535–552; Collins et al., 1994, Am. J. Trop. Med. Hyg. 51, 711–719; Narum et al., 2000, Infect. Immun. 68, 2899–2906; Anders et al., 1998, Vaccine 16, 240–247). Homologs of AMA1gene have been identified in all of the commonly studied species of *Plasmodium* (Peterson et al., 1989, Mol. Cell. Biol. 9, 3151–3154; Cheng and Saul, 1994, Mol. Biochem. Parasitol. 65, 183–187; Dutta et al., 1995, Mol. Biochem. Parasitol. 73, 267–270; Waters et al., 1990, J. Biol. Chem. 265, 17974–17979; Kocken et al., 2000, Mol. Biochem. Parasitol. 109, 147–156; Peterson et al., 1990, Mol. Biochem. Parasitol. 39, 279–284; Marshall et al., 1989, Mol. Biochem. Parasitol. 37, 281–284) and knockout studies have revealed that expression of AMA1protein is vital for the parasite survival (Triglia et al., 2000, Mol. Microbiol. 38, 706–718).

*P. falciparum* AMA1 is an integral membrane protein, synthesized as a 72 kDa (apparent molecular weight: 83 kDa) polypeptide (Peterson et al., 1989, supra), it is localized in the apical rhoptries of the merozoites present within late stage schizont (Narum and Thomas, 1994, Mol. Biochem. Parasitol. 67, 59–68). Around the time of schizont rupture and erythrocyte invasion, AMA1 of *P. falciparum* has been shown to be processed to a smaller 66 kDa protein, which is further proteolytically cleaved to 44 and 48 kDa soluble fragments (Kocken et al., 1998, J. Biol. Chem. 273, 15119–24; Howell et al., 2001, J. Biol. Chem. 276, 31311–31320). Compared to several other blood stage antigens, AMA1 of *P. falciparum*, shows limited inter-strain polymorphism (Escalante et al., 2001, Mol. Biochem. Parasitol. 113, 279–287). During natural infection, AMA1, induces both B and T-cell responses (Thomas et al., 1994, Am. J. Trop. Med. Hyg. 51, 730–740; Lal et al., 1996, Infect. Immun. 64, 1054–1059) and antibodies to both recombinant *P. falciparum* AMA1 and affinity purified naturally induced anti-AMA1 inhibit growth or invasion of *P. falciparum* parasite in vitro (Hodder et al., 2001, Infect. Immun. 69, 3286–3294). The ectodomain of AMA1 comprises a region constituting 16 inter-species conserved cysteine residues. These cysteine residues are cross-linked to form 8 disulphide bridges, which in turn, divide the ectodomain into 3 subdomains (Hodder et al., 1996, J. Biol. Chem. 271, 29446–29452). Correct folding, vis-à-vis the presence of these disulphide bonds, in the case of recombinant *P. chabaudi* and *P. falciparum* AMA1 proteins, has been shown to be critical for the induction of inhibitory anti-AMA1 antibodies (Anders et al., 1998, supra; Hodder et al., 2001, supra).

Although its function remains unclear, there is a growing need to focus resources on a human trial to evaluate the protective potential of AMA1 of *P. falciparum* in human volunteers.

Full length *P. falciparum* AMA1 was first expressed in the eukaryotic insect cell system (Narum et al., 1993, J. Chromatogr. A. 657, 357–363), although the baculovirus product was soluble, the purification strategy was not designed for scale-up production. Prokaryotic expression of AMA1 from various species has been problematic, primarily due to the formation of insoluble aggregates presumably due to incorrect folding of the protein. Previous work on *P. chabaudi* AMA1 expression in *E. coli* showed that it was necessary to include an in vitro refolding step in the process in order to obtain correctly folded protein (Anders et al., 1998, supra). A similar approach was successful for obtaining correctly folded AMA1 from *P. falciparum* and the antibodies made against it inhibited parasite growth in vitro (Hodder et al., 2001, supra). A scalable process for the production of recombinant AMA1 has not yet been described.

In this application we describe the expression of a synthetic gene encoding 449 amino acids encompassing the 3 subdomains of the AMA1 ectodomain from *P. falciparum* in *E. coli*. The protein designated as r-AMA1/E ('r' stands for recombinant and 'E' represents the *E. coli* codon bias of the synthetic gene) was refolded and purified and the final protein product was designated as AMA1/E. Biochemical characterization and evidence of correct folding of AMA1/E are presented. In addition, the in vitro parasite invasion data with antibodies raised against AMA1/E reaffirms the potential of AMA1 to be an important component of a future malaria vaccine.

SUMMARY OF THE INVENTION

Therefore, the present invention provides a method for proper expression and purification of an AMA-1 3D7 allele. The method of the present invention results in elimination of contaminating proteins and conservation of the native folding and disulfide bridging of the protein. Therefore, the essentially purified protein of the present invention retains proper conformation for optimal reactivity for vaccine and screening purposes.

The protein of the present invention is encoded by a unique DNA fragment of the ectodomain of the AMA-1 protein. Among different DNA fragments isolated from the ectodomain using polymerase chain reaction, only one nucleotide fragment encoding amino acids 83–531 of AMA-1 was found to be stable. This DNA fragment retained all 16 cysteines required for the formation of the 8 intramolecular disulphide linkages of AMA-1 but did not have the leader sequence. We were able to successfully, for the first time, express this fragment in a bacterial host and have developed a four-step purification scheme that produces >99% pure protein product, AMA1/E, which is properly folded, i.e. retains its disulfide bridges, and is stable. Furthermore, the AMA1/E protein of the present invention was found to induce a protective immune response in rabbits. This was surprising since the DNA fragment encoding the protein of the present invention did not contain a leader sequence thought to be important for immunogenicity of the protein.

Therefore, it is an object of the present invention to provide a recombinant *P. falciparum* AMA-1 protein, AMA1/E, for use as a vaccine, in diagnostic assays, and for production of antibodies.

It is another object of the present invention to provide compositions comprising purified recombinant *P. falciparum* AMA1/E.

It is yet another object of the present invention to provide novel vector constructs for recombinantly expressing *P. falciparum* AMA1/E, as well as host cells transformed with said vector.

It is also an object of the present invention to provide a method for producing and purifying recombinant *P. falciparum* AMA1/E protein comprising:

growing a host cell containing a vector expressing *P. falciparum* AMA1/E proteins in a suitable culture medium, causing expression of said vector sequence as defined above under suitable conditions for production of soluble protein and, lysing said transformed host cells and recovering said AMA1/E protein such that it retains its native folding and is essentially free of host toxins.

It is also an object of the present invention to provide diagnostic and immunogenic uses of the recombinant *P. falciparum* AMA1/E protein of the present invention, as well as to provide kits for diagnostic use for example in malaria screening and confirmatory antibody tests.

It is also an object of the present invention to provide monoclonal or polyclonal antibodies, more particularly human monoclonal antibodies or mouse monoclonal antibodies which are humanized, which react specifically with AMA1/E epitopes, either comprised in peptides or conformational epitopes comprised in recombinant proteins.

It is also an object of the present invention to provide possible uses of anti-AMA1/E monoclonal antibodies for malaria antigen detection or for therapy of chronic malaria infection.

It is yet another object of the present invention to provide a malaria vaccine comprising AMA1/E of the present invention, in an amount effective to elicit an immune response in an animal or human against *P. falciparum*; and a pharmaceutically acceptable diluent, carrier, or excipient.

It is another object of the present invention to provide a method for eliciting in a subject an immune response against malaria, the method comprising administering to a subject a composition comprising AMA1/E of the present invention. In one aspect of the invention, the AMA1/E vaccine is delivered along with an adjuvant.

It is another object of the present invention to provide a method for preventing malaria infection in an animal comprising administering to the animal the AMA1/E of the present invention.

The vaccine according to the present invention is inherently safe, is not painful to administer, and should not result in adverse side effects to the vaccinated individual.

The present invention also provides a method for fermenting and inducing the host cells, and a method for isolating and purifying the recombinant protein. Also provided is a method for bulk fermentation and expression of AMA1/E.

All the objects of the present invention are considered to have been met by the embodiments as set out below.

DETAILED DESCRIPTION

Figure 1:
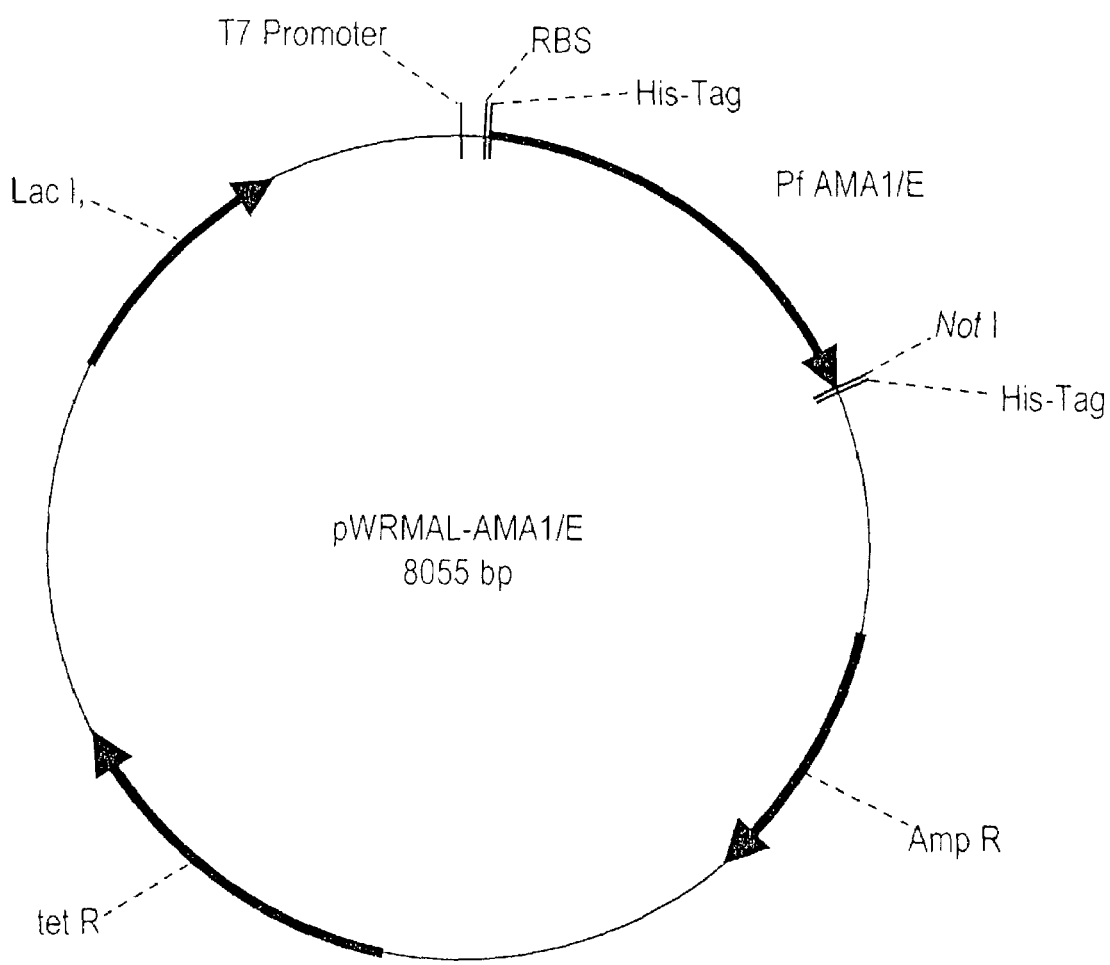
FIG. 1 is a schematic diagram of the plasmid pWRMAL containing the DNA sequence encoding *Plasmodium falciparum* AMA1/E (Pf AMA1/E).

In the description that follows, a number of terms used in recombinant DNA, parasitology and immunology are extensively utilized. In order to provide a clear and consistent understanding of the specification and claims, including the scope to be given such terms, the following definitions are provided.

In general, an 'epitope' is defined as a linear array of 3–10 amino acids aligned along the surface of a protein. In a linear epitope, the amino acids are joined sequentially and follow the primary structure of the protein. In a conformational epitope, residues are not joined sequentially, but lie linearly along the surface due to the conformation (folding) of the protein. With respect to conformational epitopes, the length of the epitope-defining sequence can be subject to wide variations. The portions of the primer structure of the antigen between the residues defining the epitope may not be critical to the structure of the conformational epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homo-oligomer or hetero-oligomer. As used herein, 'epitope' or 'antigenic determinant' means an amino acid sequence that is immunoreactive. As used herein, an epitope of a designated polypeptide denotes epitopes with the same amino acid sequence as the epitope in the designated polypeptide, and immunologic equivalents thereof. Such equivalents also include strain, subtype (=genotype), or type(group)—specific variants, e.g. of the currently known sequences or strains belonging to Plasmodium such as 3D7, FVO and CAMP, or any other known or newly defined *Plasmodium* strain.

The term 'solid phase' intends a solid body to which the individual *P. falciparum* antigen is bound covalently or by noncovalent means such as hydrophobic, ionic, or van der Waals association.

The term 'biological sample' intends a fluid or tissue of a mammalian individual (e.g. an anthropoid, a human), reptilian, avian, or any other zoo or farm animal that commonly contains antibodies produced by the individual, more particularly antibodies against malaria. The fluid or tissue may also contain *P. falciparum* antigen. Such components are known in the art and include, without limitation, blood, plasma, serum, urine, spinal fluid, lymph fluid, secretions of the respiratory, intestinal or genitourinary tracts, tears, saliva, milk, white blood cells and myelomas. Body components include biological liquids. The term 'biological fluid' refers to a fluid obtained from an organism. Some biological fluids are used as a source of other products, such as clotting factors (e.g. Factor VIII;C), serum albumin, growth hormone and the like.

The term 'immunologically reactive' means that the antigen in question will react specifically with anti-AMA-1 antibodies present in a body component from a malaria infected individual.

The term 'immune complex' intends the combination formed when an antibody binds to an epitope on an antigen.

The term 'AMA1/E' (also referred to as PfAMA/e, AMA-1/E, PfAMA-1/E, FMP2.0, FMP2.1) as used herein refers to the protein fragment or polypeptide resulting from expression of a DNA fragment encoding amino acids 83 to 531 of *P. falciparum* 3D7 AMA-1. The full length sequence of *P. falciparum* 3D7 AMA-1 has been deposited in GenBank under accession number U65407.1.

The term 'AMA1/E' as used herein also includes analogs and truncated forms that are immunologically identifiable with the native AMA-1. By 'AMA1/E' is intented AMA1/E from other strains of *Plasmodium falciparum* such as 3D7, Camp, FVO, and others, or any other newly identified strain of Plasmodium.

The term 'purified' as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of the percentage purity as used herein. An 'isolated' AMA-1 protein intends a *Plasmodium* protein composition that is at least 35% pure.

The term 'essentially purified proteins' refers to proteins purified such that they can be used for in vitro diagnostic methods and as a prophylactic compound. These proteins are substantially free from cellular proteins, vector-derived proteins or other *Plasmodium* components. The proteins of the present invention are purified to homogeneity, at least 80% pure, preferably, 90%, more preferably 95%, more preferably 97%, more preferably 98%, more preferably 99%, even more preferably 99.5%.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluveromyces, Pichia* (e.g. *Pichia pastoris*), *Hansenula* (e.g. *Hansenula polymorpha, Yarowia, Schwaniomyces, Schizosaccharomyces, Zygosaccharomyces* and the like. *Saccharomyces cerevisiae, S. carlsberoensis* and *K. lactis* are the most commonly used yeast hosts, and are convenient fungal hosts.

The term 'prokaryotes' refers to hosts such as *E. coli, Lactobacillus, Lactococcus, Salmonella, Streptococcus, Bacillus subtilis* or *Streptomyces*. Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term 'recombinant polynucleotide or nucleic acid' intends a polynucleotide or nucleic acid of genomic, cDNA, semisynthetic, or synthetic origin, which, by virtue of its origin or manipulation : (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily-be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

An 'open reading frame' (ORF) is a region of a polynucleotide sequence which encodes a polypeptide and does not contain stop codons; this region may represent a portion of a coding sequence or a total coding sequence.

A 'coding sequence' is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against malaria, whether partial or complete. A vaccine may also be useful for treatment of an infected individual, in which case it is called a therapeutic vaccine.

The term 'therapeutic' refers to a composition capable of treating malaria infection.

The term 'effective amount' for a therapeutic or prophylactic treatment refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/ antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of AMA1/E for prophylaxis of malaria disease are about 0.01 to 1000 ug/dose, more preferably about 0.1 to 100 ug/dose, most preferably about 10–50 ug/dose. Several doses may be needed per individual in order to achieve a sufficient immune response and subsequent protection against malaria.

More particularly, the present invention contemplates essentially purified AMA1/E and a method for isolating or purifying recombinant AMA1/ E protein, characterized in that the recombinantly expressed protein retains the disulfide bonds necessary for proper folding of the protein.

The AMA1/E protein of the present invention spans from amino acid 83 to 531 of AMA-1 3D7 allele (GenBank™ Accession No U65407.1). Upon expression in the parasite system (non-glycosylated), AMA1/E is believed to have an approximate molecular weight of 54 kDa as determined by reduced SDS-PAGE. The term 'AMA1/E' refers to a polypeptide or an analogue thereof (e.g. mimotopes) comprising an amino acid sequence (and/or amino acid analogues) defining at least one AMA1/E epitope. Typically, the sequences defining the epitope correspond to the amino acid sequence of AMA1/E region of P. falciparum (either identically or via substitution of analogues of the native amino acid residue that do not destroy the epitope). Other epitopes of AMA1/E include domain I defined by: amino acids 83–319 of AMA-1, domain II defined by amino acids 303–442 of AMA-1, domain III defined by amino acids 419–531 of AMA-1, and combinations of these domains such as domains I and II encompassing amino acids 83–442 of AMA-1, domains II and III encompassing amino acids 303–531 of AMA-1 and domains I and III encompassing amino acids 83–308 combined with 419–531 of AMA-1.

The AMA1/E antigen used in the present invention is preferably a full-length protein as described above, i.e. from amino acid 83 to 532 of AMA-1 3D7 allele, or a substantially full-length version, i.e. containing functional fragments thereof (e.g. fragments which are not missing sequence essential to the formation or retention of an epitope). Furthermore, the P. falciparum antigen of the present invention can also include other sequences that do not block or prevent the formation of the conformational epitope of interest. The presence or absence of a conformational epitope can be readily determined through screening the antigen of interest with an antibody as described in the Examples below (polyclonal serum or monoclonal to the conformational epitope) and comparing its reactivity to that of a denatured version of the antigen which retains only linear epitopes (if any).

The P. falciparum antigen of the present invention can be made by any recombinant method that provides the epitope of interest. For example, recombinant expression in E. coli is a preferred method to provide non-glycosylated antigens in 'native' conformation. This is most desirable because natural P. falciparum antigens are not glycosylated. Proteins secreted from mammalian cells may contain modifications including galactose or sialic acids which may be undesirable for certain diagnostic or vaccine applications. However, it may also be possible and sufficient for certain applications, as it is known for proteins, to express the antigen in other recombinant hosts such as baculovirus and yeast or higher eukaryotes, as long as glycosylation is inhibited.

The proteins according to the present invention may be secreted or expressed within compartments of the cell. Preferably, however, the proteins of the present invention are expressed within the cell and are released upon lysing the cells.

It is also understood that the isolates used in the examples section of the present invention were not intended to limit the scope of the invention and that an equivalent sequence from a P. falciparum isolate from another allele, e.g. FVO, or CAMP, can be used to produce a recombinant AMA1/E protein using the methods described in the present application. Other new strains of Plasmodium may be a suitable source of AMA-1 sequence for the practice of the present invention.

The AMA1/E protein of the present invention is expressed as part of a recombinant vector. The present invention relates more particularly to a nucleotide construct (SEQ ID NO: 1) encoding 449 amino acids of AMA-1 of P. falciparum 3D7 clone, residues 83–531. The present AMA1/E sequence was commercially synthesized with an E. coli codon bias (Retrogen, San Diego, Calif.). It would be evident to those of skill in the art that other codon bias could be used without deviating from the concept of the invention. The final protein construct (SEQ ID NO: 2) contained two histidine tags, one within the first 18 amino acids fused to the N-terminus (MAHHHHHHPGGSGSGTMH (SEQ ID NO: 3)) and the second within the 11 amino acids fused to the C-terminus (AAALEHHHHHH (SEQ ID NO: 4)). The AMA1/E sequence was cloned into a modified pET32 plasmid pWRMAL. The modifications in the plasmid include the replacement of the thioredoxin and other N-terminal tags with sequences that resulted in minimal non-AMA-1 amino acids fused to the final recombinant protein and a tet$^r$ gene for tetracycline resistance added. This plasmid comprises, in sequence, a T7 promoter, optionally a lac operator, a ribosome binding site, restriction sites to allow insertion of the structural gene and a T7 terminator sequence. Examples of other plasmids which contain the T7 inducible promoter include the expression plasmids pET-17b, pET-11a, pET-24a-d(+), pET32a, and pEt-9a, all from Novagen (Madison, Wis.); see the Novagen catalogue.

The present invention also contemplates host cells transformed with a recombinant vector as defined above. Any prokaryotic host can be used. In a preferred embodiment, E. coli strain Tuner (DE3) or strain Origami (DE3) is employed. The above plasmids may be transformed into this strain or other strains of E. coli having a DE3 background. Other host cells such as insect cells can be used depending on the vector chosen and taking into account that other cells may result in lower levels of expression.

Eukaryotic hosts include lower and higher eukaryotic hosts as described in the definitions section. Lower eukaryotic hosts include yeast cells well known in the art. Higher eukaryotic hosts mainly include mammalian cell lines known in the art and include many immortalized cell lines available from the ATCC, inluding HeLa cells, Chinese hamster ovary (CHO) cells, Baby hamster kidney (BHK) cells, PK15, RK13 and a number of other cell lines. AMA1/E expressed in these cells will be glycosylated unless the cells have been altered such that glycosylation of the recombinant protein is not possible. It is expected that when producing AMA1/E in a eukaryotic expression system, extensive investigation into methods for expressing, isolating, purifying, and characterizing the protein would be required as eukaryotic cells post-translationally modify this protein and this would alter protein structure and immunogenicity.

Methods for introducing vectors into cells are known in the art. Please see e.g., Maniatis, Fitsch and Sambrook, *Molecular Cloning; A Laboratory* Manual (1982) or *DNA Cloning*, Volumes I and II (D. N. Glover ed. 1985) for general cloning methods. Host cells provided by this invention include E. coli containing pWRMAL-AMA1/E.

A preferred method for isolating or purifying AMA1/E as defined above is further characterized as comprising:

(i) growing a host cell as defined above transformed with a recombinant vector encoding AMA1/E protein in a suitable culture medium, (ii) causing expression of said vector sequence as defined above under suitable conditions for production of a soluble protein, (iii) lysing said transformed host cells and recovering said AMA1/E protein such that it retains its native conformation and is essentially pure.

Once the host has been transformed with the vector, the transformed cells are grown in culture in the presence of the desired antibiotic, if necessary. When cells reach optimal biomass density, in this case about 0.5–2.0 O.D. 600, preferably about 0.6–1.0 O.D. 600 in small culture flasks or about 5.0–15.0 O.D. 600, preferably about 6.0–10.0 O.D. 600 in bulk fermentors, the cells are induced to produce the recombinant protein. The inventors have found after trial and error that for expression of a soluble AMA1/E in some cells, like E. coli Origami (DE3), it was necessary to cool the culture to a range of about 25–30° C., more preferably about 28° C., prior to induction. However, in other cells, like Tuner (DE3), 37° C. worked best. The concentration of inducer added, i.e. IPTG, affects maximal protein synthesis. It was found that a concentration of about 0.2 mM IPTG was best, however, a range of about 0.1 to 1.0 mM would be sufficient to produce 80–100% of maximal.

The cells were then collected and lysed to release the recombinant protein. Preferably, lysis should occur at a paste to buffer ratio of about 1 gram paste to about 5 to 10 ml of buffer w/v to reduce viscosity and volume of sample loaded on Ni-NTA column. The recombinant protein of the present invention was fused to 6-His tags at the both the N-terminal and the C-terminal since one 6-His tag at the N-terminal did not result in proper purification on the Ni column. Two 6-His tags are not advised in the field since purification of such a protein on a column usually results in a collection of breakdown products and incomplete synthesis products. However, we found that, with this protein, it is preferable to have two His-tags, one at the N-terminal and one at the C-terminal of the protein.

Preferably, lysis is in the presence of N-lauryl sarcosinate (SLS), or other mild detergent, which solubilizes and stabilizes the protein and allows for binding to the bound nickel-containing column. Even though instructions from the column manufacturer do not recommend the use of SLS, we found that such a compound facilitates the proper extraction of the recombinant protein. The mild detergent must be in a high enough concentration so that complete solubilization of the recombinant protein takes place. This initial range is between about 3% to about 7% of the total volume of the bacterial suspension. The mild detergent, used within the recommended ranges, eliminates the need for a co-solvent such as urea or guanidine, used by many other researchers. Once the bacteria are lysed and the proteins solubilized the concentration of mild detergent can be reduced by dilution; SLS can be reduced to about 0.5 to about 2%, preferably about 1.25%, for passage on to the nickel column.

Lysis is preferably at a temperature of about 4° C. to 24° C., more preferably about 4 to 15° C. in order to retain native folding of the AMA1/E protein and to reduce proteolysis. A high salt, for example sodium chloride, concentration of about 0.4–1.0 M is preferable though not necessary.

The lysate is applied over a $Ni^{+2}$-NTA affinity column in a solution containing about 1.25% mild detergent or SLS. The solution is applied at a flow rate of about 113–170 ml/min, at a cell resin to paste ratio of about 0.3–0.6 ml resin/g of paste, preferably about 0.5 ml resin/g of paste. The column is washed with a buffer containing imidazole of about 5–30 mM, preferably about 25 mM at pH of about 8.0 and reduced amount of SLS of about 0.1–0.2%, preferably about 0.125% at a pH of about 7.5–8.5, preferably about 8.0. The recombinant protein can be eluted by addition of high pH buffer of about 7.5 to about 8.5, preferably about pH 8.0, with about 400–600 mM imidazole, preferably about 500 mM of imidazole, and about 0.1–0.2%, preferably about 0.125% of SLS.

At this point the recombinant protein is about 5–10% of total protein. For refolding the protein, the $Ni^{+2}$ elution was diluted about 40 fold (v/v), rapidly, in degassed buffer containing about 0.5–3 mM, preferably about 1 mM reduced glutathione (GSH), about 0.1–0.3 mM oxidized glutathione (GSSG), preferably about 0.25, pH 8.0, and about 0.1 mM to about 5 mM EDTA. The refolding buffer was prepared fresh and refolding was carried out at room temperature (~22° C.) for a minimum of 15 h under nitrogen. The final protein product, resulting from this refolding protocol, was referred to as AMA1/E. Several other variations to the above refolding protocol were also tested. One such variation included reduction of the $Ni^{+2}$ eluted proteins with 5 mM DTT for 1 h at 37° C. before refolding.

If further purity is required, ion-exchange chromatography can be utilized. The recombinant protein in solution can be concentrated and enriched by passing through an anion exchange column of DEAE-Sepharose, in a phosphate buffer in the presence of EDTA (about 1 mM) and eluted in a phosphate buffer with EDTA and NaCl (about 100 mM) at about pH 8.0. The flow through protein is then subjected to a pH adjustment step to alter the pH of the solution such that it can be passed through a cation exchange column. The eluted AMA1/E is pH adjusted to about pH 5.7 by the addition of 1 M $NaH_2pO_4.H_2O$. Other buffers, such as HCl, can be added as is known in the art. The sample is then loaded onto a cation column, for example, SP-sepharose, preequilibrated with a sodium phosphate buffer of about 30–60 mM, preferably about 50 mM sodium phosphate, about 0.05–2.0 mM, preferably about 0.1 EDTA, about 50–150 mM, preferably about 100 mM NaCl at a pH of about 5.7. After washing the loaded column with a pH exchange buffer of about 3–6 mM, preferably about 5 mM sodium phosphate, about 0.05–2.0 mM, preferably about 0.1 mM EDTA at about pH 7.1, the AMA1/E is eluted from the column in formulation buffer: about 20–25 mM, preferably about 23.5 mM $NaH_2PO_4.H_2O$, about 30–40 mM, preferably about 37.5 mM NaCl, about 0.05–2.0 mM, preferably about 0.1 mM EDTA at about pH 7.1. NaCl concentration in this SP elution buffer can be as high 150 mM NaCl, which yields approxamately 20% more AMA1/E but then the final product may have to be dialysed against formulation buffer to lower the salt concentration if that is required.

The pH adjustement step is unique and discouraged in the art: changing the charge of a protein from above to below its isoelectric point (5.98) could have caused the protein to separate into a non-soluble form. However, the proteins remains soluble under these conditions. Others usually use size exclusion, instead of cation exchange chromatography, to achieve the next degree of purity, however, this presents serious limitation when designing a process for bulk production of the protein.

The bulk process for the isolation of purified AMA1/E differs little from the process described above.

The present invention also relates to a composition comprising peptides or polypeptides as described above, for in vitro detection of malaria antibodies present in a biological sample.

The present invention also relates to a composition comprising at least one of the following AMA-1 conformational epitopes and peptides retaining these epitopes:

epitope recognized by monoclonal antibodies 4G2 (from Alan Thomas, Primate Research Institute, The Netherlands), domain I defined by: amino acids 83–319 of AMA-1, domain II defined by amino acids 303–442 of AMA-1, domain III defined by amino acids 419–531 of AMA-1, and combinations of these domains such as domains I and II encompassing amino acids 83–442 of AMA-1, domains II and III encompassing amino acids 303–531 of AMA-1 and domains I and III encompassing amino acids 83–308 combined with 419–531 of AMA-1.

The present invention also relates to a method for in vitro diagnosis of malaria antibodies present in a biological sample, comprising at least the following steps (i) contacting said biological sample with a composition comprising any of the AMA1/E peptides as defined above, preferably in an immobilized form under appropriate conditions which allow the formation of an immune complex, wherein said peptide or protein can be a biotinylated peptide or protein which is covalently bound to a solid substrate by means of streptavidin or avidin complexes, (ii) removing unbound components, (iii) incubating the immune complexes formed with heterologous antibodies, with said heterologous antibodies having conjugated to a detectable label under appropriate conditions, (iv) detecting the presence of said immune complexes visually or mechanically (e.g. by means of densitometry, fluorimetry, colorimetry).

The present invention also relates to a kit for determining the presence of malaria antibodies, in a biological sample, comprising:

at least one peptide or protein composition as defined above, possibly in combination with other polypeptides or peptides from Plasmodium or other types of malaria parasite, with said peptides or proteins being preferentially immobilized on a solid support, more preferably on different microwells of the same ELISA plate, and even more preferentially on one and the same membrane strip, a buffer or components necessary for producing the buffer enabling binding reaction between these polypeptides or peptides and the antibodies against malaria present in the biological sample, means for detecting the immune complexes formed in the preceding binding reaction, possibly also including an automated scanning and interpretation device for inferring the malaria parasite present in the sample from the observed binding pattern.

The immunoassay methods according to the present invention utilize AMA1/E domains that maintain linear (in case of peptides) and conformational epitopes (proteins) recognized by antibodies in the sera from individuals infected with a malaria parasite. The AMA1/E antigens of the present invention may be employed in virtually any assay format that employs a known antigen to detect antibodies. A common feature of all of these assays is that the antigen is contacted with the body component suspected of containing malaria antibodies under conditions that permit the antigen to bind to any such antibody present in the component. Such conditions will typically be physiologic temperature, pH and ionic strenght using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon.TM.), diazotized paper, nylon membranes, activated beads, and Protein A beads. For example, Dynatech Immunolon.TM.1 or Immunolon.TM. 2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are know in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of malaria antibodies in the antibody-antigen complexes is directly monitored. This may be accomplished by determining whether labeled anti-xenogeneic (e.g. anti-human) antibodies which recognize an epitope on anti-malaria antibodies will bind due to complex formation. In a competitive format, the amount of malaria antibodies in the sample is deduced by monitoring the competitive effect on the binding of a known amount of labeled antibody (or other competing ligand) in the complex.

Complexes formed comprising anti-malaria antibody (or in the case of competitive assays, the amount of competing antibody) are detected by any of a number of known techniques, depending on the format. For example, unlabeled malaria antibodies in the complex may be detected using a conjugate of anti-xenogeneic Ig complexed with a label (e.g. an enzyme label).

In an immunoprecipitation or agglutination assay format the reaction between the malaria antigens and the antibody forms a network that precipitates from the solution or suspension and forms a visible layer or film of precipitate. If no anti-malaria antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles. However, gelatin particles may also be used. The assays utilizing either of these carriers are based on passive agglutination of the particles coated with purified antigens.

The AMA1/E proteins, peptides, or antigens of the present invention will typically be packaged in the form of a kit for use in these immunoassays. The kit will normally contain in separate containers the AMA1/E antigen, control antibody formulations (positive and/or negative), labeled antibody when the assay format requires the same and signal generating reagents (e.g. enzyme substrate) if the label does not generate a signal directly. The AMA1/E antigen may be already bound to a solid matrix or separate with reagents for binding it to the matrix. Instructions (e.g. written, tape, CD-ROM, etc.) for carrying out the assay usually will be included in the kit.

Immunoassays that utilize the AMA1/E antigen are useful in screening blood for the preparation of a supply from which potentially infective malaria parasite is lacking. The method for the preparation of the blood supply comprises: reacting a body component, preferably blood or a blood component, from the individual donating blood with AMA1/E proteins of the present invention to allow an immunological reaction between malaria antibodies, if any, and the AMA1/E antigen, and detecting whether anti-malaria antibody—AMA1/E antigen complexes are formed as a result of the reacting. Blood contributed to the blood supply is from donors that do not exhibit antibodies to the AMA1/E antigens.

The present invention further contemplates the use of AMA1/E proteins, or parts thereof as defined above, for in vitro monitoring malaria infection or prognosing the response to treatment (for instance with chloroquine, mefloquine, Malarome) of patients suffering from malaria infection comprising:

incubating a biological sample from a patient with malaria infection with an AMA1/E protein or a suitable part thereof under conditions allowing the formation of an immunological complex, removing unbound components, calculating the anti-AMA1/E titers present in said sample (for example at the start of and/or during the course of therapy), monitoring the natural course of malaria infection, or prognosing the response to treatment of said patient on the basis of the amount anti-AMA1/E titers found in said sample at the start of treatment and/or during the course of treatment.

Patients who show a decrease of 2, 3, 4, 5, 7, 10, 15, or preferably more than 20 times of the initial anti-AMA1/E titers could be concluded to be long-term, sustained responders to malaria therapy.

It is to be understood that smaller fragments of the above-mentioned peptides also fall within the scope of the present invention. Said smaller fragments can be easily prepared by chemical synthesis and can be tested for their ability to be used in an assay as detailed above.

The present invention also relates to a kit for monitoring malaria infection or prognosing the response to treatment (for instance to medication) of patients suffering from malaria infection comprising:

at least one AMA1/E peptide as defined above, a buffer or components necessary for producing the buffer enabling the binding reaction between these proteins or peptides and the anti-AMA1/E antibodies present in a biological sample, means for detecting the immune complexes formed in the preceding binding reaction, possibly also an automated scanning and interpretation device for inferring a decrease of anti-AMA1/E titers during the progression of treatment.

The present invention also relates to a serotyping assay for detecting one or more serological types or alleles of malaria parasite present in a biological sample, more particularly for detecting antibodies of the different types or alleles of malaria parasites to be detected combined in one assay format, comprising at least the following steps:

(i) contacting the biological sample to be analyzed for the presence of malaria antibodies of one or more serological types, with at least one of the AMA1/E compositions as defined above, preferentially in an immobilized form under appropriate conditions which allow the formation of an immune complex, (ii) removing unbound components, (iii) incubating the immune complexes formed with heterologous antibodies, with said heterologous antibodies being conjugated to a detectable label under appropriate conditions, (iv) detecting the presence of said immune complexes visually or mechanically (e.g. by means of densitometry, fluorimetry, calorimetry) and inferring the presence of one or more malaria serological types present from the observed binding pattern.

It is to be understood that the compositions of proteins or peptides used in this method are recombinantly expressed type-specific or allele-specific proteins or type-specific peptides.

The present invention further relates to a kit for serotyping one or more serological types or alleles of malaria parasite present in a biological sample, more particularly for detecting the antibodies to these serological types of malaria parasites comprising:

at least one AMA1/E protein or AMA1/E peptide, as defined above, a buffer or components necessary for producing the buffer enabling the binding reaction between these proteins or peptides and the anti-AMA1/E antibodies present in a biological sample, means for detecting the immune complexes formed in the preceding binding reaction, possibly also an automated scanning and interpretation device for detecting the presence of one or more serological types present from the observed binding pattern.

The present invention also relates to the use of a peptide or protein composition as defined above, for immobilization on a solid support and incorporation into a reversed phase hybridization assay, preferably for immobilization as parallel lines onto a solid support such as a membrane strip, for determining the presence or the genotype of malaria parasite according to a method as defined above. Combination with other type-specific or allele-specific antigens from other malaria parasites also lies within the scope of the present invention.

The present invention further relates to an AMA-1 specific antibody raised upon immunizing an animal with a peptide or protein composition of the present invention, with said antibody being specifically reactive with any of the polypeptides or peptides as defined above, and with said antibody being preferably a monoclonal antibody.

The present invention also relates to an AMA1/E or AMA-1 specific antibody screened from a variable chain library in plasmids or phages or from a population of human B-cells by means of a process known in the art, with said antibody being reactive with any of the polypeptides or peptides as defined above, and with said antibody being preferably a monoclonal antibody.

The AMA1/E specific monoclonal antibodies of the invention can be produced by any hybridoma liable to be formed according to classical methods from splenic or lymph node cells of an animal, particularly from a mouse or rat, immunized against the *Plasmodium* polypeptides or peptides according to the invention, as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains from cDNA or genomic clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with malaria, or vaccinated against malaria. Such human monoclonal antibodies are prepared, for instance, by means of human peripheral blood lymphocytes (PBL) repopulation of severe combined immune deficiency (SCID) mice, or by means of transgenic mice in which human immunoglobulin genes have been used to replace the mouse genes.

The invention also relates to the use of the proteins or peptides of the invention, for the selection of recombinant antibodies by the process of repertoire cloning.

Antibodies directed to peptides or single or specific proteins derived from a certain strain may be used as a medicament, more particularly for incorporation into an immunoassay for the detection of *Plasmodium* strains for detecting the presence of AMA-1 antigens, or antigens containing AMA-1, or AMA1/E epitopes, for prognosing/monitoring of malaria disease, or as therapeutic agents.

Alternatively, the present invention also relates to the use of any of the above-specified AMA1/E monoclonal antibodies for the preparation of an immunoassay kit for detecting the presence of AMA-1 antigen or antigens containing AMA1/E epitopes in a biological sample, for the preparation of a kit for prognosing/monitoring of malaria disease or for the preparation of a malaria medicament.

The present invention also relates to a method for in vitro diagnosis or detection of malaria antigen present in a biological sample, comprising at least the following steps:

(i) contacting said biological sample with any of the AMA1/E specific monoclonal antibodies as defined above, preferably in an immobilized form under appropriate conditions which allow the formation of an immune complex, (ii) removing unbound components, (iii) incubating the immune complexes formed with heterologous antibodies, which specifically bind to the antibodies present in the sample to be analyzed, with said heterologous antibodies conjugated to a detectable label under appropriate conditions, (iv) detecting the presence of said immune complexes visually or mechanically (e.g. by means of densitometry, fluorimetry, colorimetry).

The present invention also relates to a kit for in vitro diagnosis of a malaria antigen present in a biological sample, comprising:

at least one monoclonal antibody as defined above, with said antibody being preferentially immobilized on a solid substrate, a buffer or components necessary for producing the buffer enabling binding reaction between these antibodies and the malaria antigens present in the biological sample, and a means for detecting the immune complexes formed in the preceding binding reaction.

The kit can possibly also include an automated scanning and interpretation device for inferring the malaria antigens present in the sample from the observed binding pattern.

Monoclonal antibodies according to the present invention are suitable both as therapeutic and prophylactic agents for treating or preventing malaria infection in susceptible malaria-infected subjects. Subjects include rodents such as mice or guinea pigs, monkeys, and other mammals, including humans.

In general, this will comprise administering a therapeutically or prophylactically effective amount of one or more monoclonal antibodies of the present invention to a susceptible subject or one exhibiting malaria infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before parasite can be controlled, and the induced immune response to the MAbs in the subject does not induce "serum sickness" in the subject. Preferably, the MAbs administered exhibit some secondary functions such as binding to Fc receptors of the subject.

Treatment of individuals having malaria infection may comprise the administration of a therapeutically effective amount of AMA1/E antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to AMA1/E, or an antibody capable of protecting against malaria in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg- 1 ug/kg, 1 ug/kg- 100 ug/kg, 100 ug/kg-500 ug/kg, 500 ug/kg- 1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered.

In a similar approach, another prophylactic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-AMA1/E response (Linthicum, D. S. and Farid, N. R., Anti-Idiotypes, Receptors, and Molecular Mimicry (1988), pp 1–5 and 285–300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cyteine and derivatives thereof. Alternative protein modification techniques may be used e.g., $NH_2$-acetylation or COOH-terminal amidation, to provide additional means for coupling or fusing the peptide to another protein or peptide molecule or to a support.

The antibodies capable of protecting against malaria are intended to be provided to recipient subjects in an amount sufficient to effect a reduction in the malaria infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

The present invention more particularly relates to a composition comprising at least one of the above-specified peptides or a recombinant AMA1/E protein composition as defined above, for use as a vaccine for immunizing a mammal, preferably humans, against malaria, comprising administering a sufficient amount of the composition possibly accompanied by pharmaceutically acceptable adjuvant(s), to produce an immune response.

Immunogenic compositions can be prepared according to methods known in the art. The present compositions comprise an immunogenic amount of a recombinant AMA1/E proteins or peptides as defined above, usually combined with a pharmaceutically acceptable carrier, preferably further comprising an adjuvant.

The proteins of the present invention, preferably purified AMA1/E derived from (3D7), are expected to provide a particularly useful vaccine antigen, since the antigen is able to induce invasion inhibitory antibodies as well as high titer antibodies that react with schizont-infected erythrocytes.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to montanide, aluminum hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine (nor-MDP), N-acetylmuramyl-L-alanyl-D-isoglutaminyl-L-alanine-2-(1'2'-dipalmitoyl-sn-glycero-3-hydroxyphosphoryl and RIBI, which contains three components extracted from bacteria, monophosphoryl lipid A, trehalose dimycolate, and cell wall skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, Mass.) or SAF-1 (Syntex) may be used. Further, Complete Freund's Adjuvant (CFA) and Incomplete Freund's Adjuvant (IFA) may be used for non-human applications and research purposes. Other adjuvants for human research include AS01, AS01B, AS02A, AS02V, and AS03, AS04, AS05 (GlaxoSmith Kline, Pa.), among others known or newly discovered.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. The AMA1/E proteins of the invention may also be incorporated into Immune Stimulating Complexes together with saponins, for example QuilA (ISCOMS).

Immunogenic compositions used as vaccines comprise a 'sufficient amount' or 'an immunologically effective amount' of the proteins of the present invention, as well as any other of the above mentioned components, as needed. 'Immunologically effective amount', means that the administration of that amount to an individual, either in a single dose or as part of a series, is effective for treatment, as defined above. This amount varies depending upon the health and physical condition of the individual to be treated, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, the strain of malaria infection, and other relevant factors. It is expected that the amount will fall in a relatively broad range that can be determined through routine trials. Usually, the amount will vary from 0.01 to 1000 ug/dose, more particularly from about 1.0 to 100 ug/dose most preferably from about 10 to 50 ug/dose.

The proteins may also serve as vaccine carriers to present homologous (e.g. other malaria antigens, such as $MSP-1_{42}$ CSP, TRAP, LSA1, LSA3, Pfs25) or heterologous (non-malaria) antigens. In this use, the proteins of the invention provide an immunogenic carrier capable of stimulating an immune response to other antigens. The antigen may be conjugated either by conventional chemical methods, or may be cloned into the gene encoding AMA1/E fused to the 5' end or the 3' end of the AMA1/E gene. The vaccine may be administered in conjunction with other immunoregulatory agents.

The compounds of the present invention can be formulated according to known methods to prepare pharmaceutically useful compositions, whereby these materials, or their functional derivatives, are combined in admixture with a phamaceutically acceptable carrier vehicle. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the compounds, whether antibodies or vaccines, disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1–10 separate doses, followed by other doses given at subsequent time intervals required to maintain and or reinforce the response, for example, at 1–4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container means containing the vaccine or antibodies of the invention. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Cloning and expression: A nucleotide construct encoding 449 amino acids of AMA1of *P. falciparum* 3D7 clone, residue # $83_{Gly}$–$531_{Glu}$ was commercially synthesized with an *E. coli* codon bias (Retrogen, San Diego, Calif.). The synthetic gene insert was ligated to the Nco I and Not I sites of a modified pET32 plasmid, called PWRMAL. The modifications in the plasmid include the replacement of the thioredoxin and other N-terminal tags with sequences that resulted in minimal non-AMA1amino acids fused to the final recombinant protein and a $tet^r$ gene for tetracycline resistance added. (Angov, E. et al.; unpublished). To correct a reading frame error the recombinant vector was cut with Nco I, end-filled with Klenow fragment and religated. The final construct contained 18 amino acids fused to the N-terminus and 11 amino acids fused to the C-terminus. The resulting protein construct was designated as r-AMA1/E (MAHHHHHHPGGSGSGTMH (SEQ ID NO: 3))-(AMA1 amino acids # 83–531)-AAALEHHHHHH (SEQ ID NO: 4)). The recombinant plasmid, pWRMAL-AMA1/E (FIG. 1) was transformed into *E. coli* Sure II cells and the insert was sequenced on both strands. For protein expression the recombinant plasmid was transformed into a 'redox modified' host *E. coli* strain (Origami (DE3); Novagen, Madison, Wis.). Origami (DE3) cells are tetracycline and kanamycin resistant. Expression of r-AMA1/E protein was confirmed by IPTG induction in shake flask cultures and glycerol stocks were prepared.

Fermentation (GMP production): Expression of r-AMA1/E protein was carried out in a 10 L bioreactor (New Brunswick Scientific, Edison, N.J.) at the lab scale and in a 300 L bioreactor (New Brunswick Scientific, Edison, N.J.) at the Walter Reed Army Institute of Research Pilot Bioproduction Facility. Medium consisting of Super Broth containing 0.8% glycerol and 12.5 µg ml$^{-1}$ tetracycline was inoculated with a 3 L overnight culture started from a Production Seed Lot #0788. The bioreactor temperature was maintained at 27° C.; pH 7.2 and agitation at 400 rpm. At a cell density $OD_{600}$=7.0, IPTG was added, to a final concentration of 0.1 mM. One hour later cells were harvested by centrifugation and frozen at −80° C. Aliquots (10 to 150 g)

from this production were used to develop a purification and refolding process of r-AMA1/E protein at the lab prior to scale-up (1500 g) in a GMP environment.

Plasmid Stability: The presence of recombinant plasmid in *E. coli* Origami (DE3) cells after fermentation was determined by plating an appropriate dilution of cells on LB agar plates containing either tetracycline (12.5 µg ml$^{-1}$) or ampicillin (100 µg ml$^{-1}$) (selective plates) and on LB agar plates containing no antibiotic (non-selective plates). The percent plasmid retention [No. colonies on selective plates/ No. colonies on non-selective plates] was calculated using colony counts on appropriate dilution plates containing between 30 and 300 colonies.

Metal affinity purification (Lab-scale): All buffers were endotoxin free and maintained chilled; all chemicals used during purification were ACS certified or the next best available grade. Purification was carried out at room temperature on a Waters-600 liquid chromatography system configured to run Pharmacia-Amersham HR columns. Cell paste was thawed and suspended in 5 times w/v of buffer-A (15 mM $Na_2HPO_4$, 5.1 mM $KH_2PO_4$, 450 mM NaCl; pH 7.4) and mixed until homogenous. A solution of 20% sodium N-lauroyl sarcosine (sarkosyl) was added to a final concentration of 5% detergent. This suspension was mixed and the *E. coli* cells were disrupted by high-pressure microfluidization (Model 1109, Microfluidic Corp., Newton, Mass.). The cell lysate was cleared by centrifugation at 22,000 xg and the supernatant was diluted 4 fold in buffer-A before loading onto a $Ni^{+1}$-NTA Superflow column (Qiagen, Valencia, Calif.; 0.5 ml packed resin per gram paste). The $Ni^{+2}$ column was pre-equilibrated with buffer-B (buffer-A containing 1.25% sarkosyl; pH 7.4). After loading the lysate, the $Ni^{+2}$ column was washed with 20 column volumes (CV) of the buffer-C (buffer-A with 10 mM imidazole, 0.125% sarkosyl; pH 7.4) followed by 20 CV of buffer-D (20 mM sodium phosphate, 25 mM imidazole, 0.125% sarkosyl; pH 8.0). Bound proteins were eluted from the column in buffer-D containing 500 mM imidazole (pH 8.0).

Refolding: The $Ni^{+2}$ elution was diluted 40 fold (v/v), rapidly, in degassed buffer-E (20 mM sodium phosphate, 1 mM EDTA, 1 mM reduced glutathione (GSH), 0.25 mM oxidized glutathione (GSSG); pH 8.0). The refolding buffer was prepared fresh and refolding was carried out at room temperature (~22° C.) for a minimum of 15 h under nitrogen. The final protein product, resulting from this refolding protocol, was referred to as AMA1/E. Several other variations to the above refolding protocol were also tested. One such variation included reduction of the $Ni^{+2}$ eluted proteins with 5 mM DTT for 1 h at 37° C. before refolding. The protein after reduction and refolding followed by ion-exchange purification was referred to as RR-AMA1/E.

Ion-exchange purification: Ion-exchange column resins were sanitized with 0.2 N NaOH before use and then equilibrated to initial binding conditions. After the refolding step, AMA1/E protein was concentrated on a DEAE Sepharose anion-exchange column (Amersham Pharmacia Biotech, Piscataway, N.J.); 0.25 ml packed resin per gram paste), the column was pre-equilibrated with buffer-E without the GSH/GSSG. After loading the protein, the column was washed with a minimum of 30 CV of the same equilibration buffer followed by 10 CV of buffer-F (5 mM sodium phosphate, 50 mM NaCl, 1 mM EDTA; pH 8.0). AMA1/E was eluted in buffer-F containing a final concentration of 100 mM NaCl (pH 8.0). AMA1/E eluted from the DEAE column was pH adjusted to 5.7 by the addition of 1M $NaH_2PO_4.H_2O$ and loaded on a SP Sepharose cation-exchange column (Amersham Pharmacia Biotech; 0.15 ml packed resin per gram paste), pre-equilibrated with buffer-G (50 mM sodium phosphate, 0.1 mM EDTA, 100 mM NaCl; pH 5.7). The column was washed with 20 CV of buffer-G containing a final 275 mM NaCl (pH 5.7), followed by 10 CV of a pH exchange buffer (5 mM sodium phosphate, 0.1 mM EDTA; pH 7.1). AMA1/E was eluted from the column in formulation buffer (23.5 mM $NaH_2PO_4.H_2O$, 37.5 mM NaCl, 0.1 mM EDTA; pH 7.1).

Formulation, lyophilization and storage: Purified AMA1/E protein eluted from the SP column was quantified by Bio-Rad DC protein assay (BioRad, Richmond, Calif.). AMA1/E was vialed at 100 µg ml$^{-1}$, 65 µg protein per vial, in the final formulation buffer (23.5 mM $NaH_2PO_4.H_2O$, 30 mM NaCl, 0.1 mM EDTA, 3.15% sucrose; pH 7.1) and lyophilized.

Residual sarkosyl and endotoxin content determination: The residual sarkosyl in purified AMA1/E protein preparations was measured by a reversed-phase HPLC method (Burgess, R. R., 1996, Meth. Enzymol. 273, 145–149). Endotoxin content was estimated using the chromogenic Limulus Amebocyte Lysate (LAL) endpoint assay (Associates of Cape Cod, Falmouth, Mass.). Dilutions of all protein samples and LAL standard were prepared in pyrogen-free vials. Positive control solutions prepared for the standard curves ranged from 1 endotoxin unit (EU) ml$^{-1}$ to 0.06 EU ml$^{-1}$, in two-fold serial dilutions. A 96-well plate heater was used for incubation at 37° C. for 20 min and the assay was carried out as per the manufacturer's instruction. The plates were read at 405 nm on $V_{max}$ kinetic microplate reader (Molecular Devices Corp., Sunnyvale, Calif.).

Purity and stability analysis: AMA1/E was evaluated for purity on precast polyacrylamide gels (4–12% gradient Bis-Tris, Invitrogen, Carlsbad, Calif.), run under reduced and non-reduced conditions, with 5–10 µg protein loaded per well. Gels were stained with Coomassie blue, destained, scanned on a Laser densitometer and acquired data was analyzed by ImageQuant 5.1 software (Molecular Dynamics, Sunnyvale, Calif.). Residual host cell protein (HCP) content, was assessed by ELISA and Western blotting, using commercially available kits (Cygnus Technologies, Plainville, Mass.). The HCP standard recommended by the manufacturer was used. In addition to this control, a lysate of the host *E. coli* Origami (DE3) (expressing a *P. vivax* MSP1 protein construct) was also tested as a standard between 1000 and 15 ng ml$^{-1}$ protein concentration, to determine if the kit was capable of detecting proteins from this specific host *E. coli*. The total protein in the Origami (DE3) lysate was estimated by BCA protein assay (Pierce). HCP ELISA was performed twice, using concentrations of AMA-1/E, between 10,000 and 80 ng ml$^{-1}$, as per the 'standard procedure' recommended by the manufacturer. Immunoblotting for HCP determination (Cygnus Technologies kit) was carried out using the HCP standard provided by the manufacturer and also using the Origami (DE3) *E. coli* lysate, between 4000 and 250 ng protein per well run on a reducing gel. The proteins were electrophoretically transferred to a nitrocellulose membrane and the western blot assay was performed as per the manufacturer's instructions. Stability of AMA1/E was determined by SDS-PAGE and western blotting of protein samples drawn monthly from aliquots stored at −80° C., −30° C., 4° C., 22° C. (RT) and 37° C.

Primary structure analysis: Purified AMA1/E protein was sequenced by automated Edman's degradation method on an Applied Biosystems model 477A protein sequencer, in-line with a HPLC (Applied Biosystems model 120A), for detection of phenylthiohydantoin-derived amino acids. Protein samples were analyzed by, Matrix Assisted Laser Desorption Ionization-Time of flight mass spectrometer (MALDI-TOF; Voyager Biospectrometry RP system, Applied Biosystems), using Sinapinic acid matrix. Lysozyme and Cytochrome C were used as mass standards.

Reduction, alkylation and free thiol analysis: AMA1/E protein was reduced with a 100-fold molar excess of DTT over cysteines in presence of either 4 M urea (for SDS-PAGE) or 4 M guanidine-HCl (for RP-HPLC and Ellman's test) at 50° C. for 1 h. Alkylation was carried out in presence of either 4 M urea or 4 M guanidine-HCl, along with 1000-fold molar excess of iodoacetamide over cysteines, for 1 h at room temperature in the dark. Free sulfhydryl groups were estimated in the presence and absence of 4 M guanidine-HCl by Ellman's reagent (5,5'-dithio-bis-3-nitrobenzoic acid) (Ellman, G. L., 1959, Arch. Biochem. Biophys. 82, 50–77). L-cysteine was used to plot the standard curve.

Gel-permeation (GPC) and reversed-phase (RPC) chromatography: HPLC analysis of purified protein was carried out using a Waters-510 HPLC pump, connected to Waters-712 WISP autosampler and controlled by Millenium Release 3.2 chromatographic software (Waters Corp., Milford, Mass.). Waters-996 PDA detector was used to monitor the elution profiles. For GPC analysis a Shodex Protein KW-803 column (Waters Corp., Milford, Mass.) was used with 10 µg protein injection. Buffer system consisted of 20 mM sodium phosphate, 100 mM $K_2SO_4$ (pH 7.15) at 0.5 ml min$^{-1}$ flow rate. The column was calibrated with molecular weight standards (BioRad). RPC analysis was done with a C8 Aquapore RP-300 Å column, 7µ, 30_2.1 mm (PE Brownlee, Norwalk, Conn.) at 0.5 ml min$^{-1}$ flow-rate and 4–12 µg protein per load. Solvent A: 0.05% trifluroacetic acid (TFA) in $H_2O$; solvent B: 0.05% TFA in acetonitrile. The solvent gradient consisted of 100% solvent A for 5 min, 100% to 30% solvent A over 15 min, 30% to 0% solvent A over 5 min and back to 100% solvent A over 5 min.

Immune reagents: Rat monoclonal antibody, 4G2dc1 (used at 1.5 µg ml$^{-1}$ on immunoblots and ELISA), recognizes a disulphide bond dependent conformational epitope on P. falciparum AMA1(Kocken, et al., 1998, supra), was kindly provided by Dr. Alan W. Thomas, Biomedical Primate Research Center, Rijswijk, The Netherlands. A pool of immune human sera (used at 1:1000 dilution on immunoblots) was collected from an endemic area in Western Kenya; the same dilution of a pool of commercially obtained normal human serum (The Binding Site Limited, Birmingham, UK) was used as a negative control.

Immunoblotting: Proteins were separated on SDS-PAGE and electrophoretically transferred to a nitrocellulose membrane (Towbin et al., 1979, Biotechnology 24, 145–149). The blot was blocked with 0.5% casein and 0.3% Tween-20 containing phosphate buffered saline (PBS). Appropriate dilution of primary antibody in PBST (PBS with 0.05% Tween-20) was incubated for 2 h. The blot was washed with PBST and then incubated with 1:5000 dilution of HRP conjugated secondary antibody (Southern Biotechnology Associates, Birmingham, AL) for 1 h. After washing with PBST, the blot was developed either with Super Signal Chemiluminescent substrate (Pierce, Rockford, Ill.) or with BM Blue POD substrate (Roche, Indianapolis, Ind.) according to the manufacturer's recommendation.

Indirect-immumofluorescence assay (IFA): Recognition of P. falciparum 3D7 schizonts, by anti-AMA1antibodies was tested by IFA. Thin blood smears were fixed with chilled methanol and serial dilutions of sera in PBST were incubated for 2 h. Slides were washed three times with PBST and incubated with a 1:100 dilution of goat anti-rabbit IgG FITC-labeled antibodies (Southern Biotechnologies Associates) for 1 h. Slides were washed, anti-fade solution (Molecular Probes, Inc, Eugene, Oreg.) was applied and read on a UV fluorescence microscope. IFA titers were determined as the last serum dilution with a positive recognition of the parasite compared to the negative adjuvant control rabbit serum diluted 1:20. The assay was done twice on separate days.

Rabbit Immunization and total IgG purification: Groups of three NZW rabbits were immunized, three times with 100 µg of lab-grade refolded AMA1/E (animal codes R-1, 2, 3); reduced and refolded protein RR-AMA1/E (R-4, 5, 6) or its reduced and alkylated form RA-AMA1/E (R-7, 8, 10). A group of 3 rabbits received 50 µg (V-2, 3, 4) or 100 µg (V-9, 10, 11) of AMA1/E protein produced under GMP environment. A control group of 3 rabbits (R-9, V45, 45) were given PBS along with the adjuvant. Formulation was prepared by adding 70% (v/v) Montanide® ISA-720 (Seppic Inc. Paris, France) to 30% antigen to make a total 1 ml emulsion per dose. The immunization was given subcutaneous at multiple sites, with a three wk interval between consecutive immunizations. Serum samples were collected 2 wk after each immunization. Rabbits were bled out 2 wk after the last immunization. Total IgG was purified from 9 ml pooled rabbit sera (lab-grade AMA1/E and RA-AMA1/E group). The adjuvant control IgG was purified from a single animal (R9). IgG purification was done on a 5 ml protein-G Sepharose column (Amersham Pharmacia Biotech. Piscataway, N.J.) using IgG binding and elution buffers (Pierce, Rockford, Ill.), according to the manufacturer's recommendation.

ELISA: Antibody response was evaluated by enzyme-linked immunosorbent assay (ELISA). Ninety six well microtiter plates (Dynax, Chantilly, Va.) were coated with 100 ng per well of either RA-AMA1/E or AMA1/E, incubated overnight at 4° C., plates were blocked for 1 h with PBST containing 5% casein (Sigma, St. Louis, Mo.) and washed with PBST. Consecutive dilutions of individual rabbit sera were incubated for 2 h at room temperature. Plates were washed and 1:4000 diluted HRP-conjugated secondary antibody was incubated for 1 h. Plates were washed and developed for 25 min with ABTS-peroxidase substrate (Kirkegaard & Perry Laboratories, Gaithersburg, Md.). $OD_{405}$ was recorded and comparative ELISA titers were calculated using regression analysis on the titration curve. The ELISA was repeated 3 times for each individual serum, in triplicate wells, on separate days. Competitive ELISA was carried out using sera from 3 rabbits immunized with lab-grade AMA1/E and two rabbits in the RA-AMA1/E group. The sera were diluted 1:1000 and pre-incubated in solution with 15 µg ml$^1$ of either AMA1/E or RA-AMA1/E or with BSA, overnight at 4° C. on a shaker. The tubes were centrifuged at 15,000 rpm for 15 min and the supernatants were analyzed by ELISA (as described above), with AMA1/E coated on plates. The competition assay was done 3 times.

Parasite culture and Growth Inhibition Assay (GIA): P. falciparum clone 3D7 cultures were prepared as described previously (Haynes et al., 2002, Erythrocytic Malaria Growth or Invasion Inhibition Assays (GIA) with Emphasis on Suspension Culture GIA, Chapter 51, in Malaria Methods and Protocols, ed. Denise L. Doolan, Methods in Molecular Medicine, The Humana Press Inc., N.J.), in 48-well plates, kept in suspension cultures angled on a rotator platform or under static conditions. All cultures contained a final 10% heat inactivated normal human serum in bicarbonate-containing RPMI 1640. Plates were gassed with 5% $O_2$, 5% $CO_2$ and heat-sealed in plastic bags. Synchronized cultures adjusted to 0.2% late ring stages were mixed with test or control serum or IgG (dialyzed into RPMI-NaOH) to a final hematocrit of 4%. In order to assess the antigen specificity of the antibody mediated inhibitions, antigens (AMA1/E or RA-AMA1/E) were added to the IgG preparations before testing in the GIA. The final concentration of antigens in the GIA was 5.3 µg ml$^{-1}$ (limited by low solubility of RA-AMA1/E protein). Merozoites were released after approximately 34 h and developing ring stages were harvested 14 h post invasion, stained with Hoechst dye-33342 and analyzed by flow-cytometry (Haynes et al., 2002, supra). The fluorescence signal was determined for a minimum of 40,000 erythrocytes gated on forward scatter. The fluorescent signal of ring-infected erythrocytes was about 20 times that of uninfected erythrocytes and schizont-infected erythrocytes, if present, had another 20-fold increase in signal. Almost all (>99%) of the parasites harvested from the assays were ring forms or early trophozoite stages, as confirmed by spot checks of Giemsa-stained thin smears. Percentage inhibition was calculated from the mean parasitaemia of triplicate test and control wells as 100% —(test/control). Sera from rabbits immunized with the adjuvant and PBS were used as controls in the GIA. Prebleeds from individual rabbits was also tested.

Statistical analysis: Microsoft Excel was used to calculate the p values for 2-tailed t tests and the correlation coefficients ($R^2$)

EXAMPLE 1

Fermentation of *E. coil* Origami (DE3) expressing the r-AMA1/E protein at 10L and 300L scale: The synthetic gene cloned in the vector pWRMAL was sequenced and the translation of this gene sequence revealed no amino acid changes from the published 3D7 clone sequence (GenBank™ Accession No U65407.1, SEQ ID NO:6). Fermentation conditions were developed in a 10 L bioreactor and later scaled-up to a 300 L GMP fermentation. The 10 L fermentation routinely resulted in 150 gm cell paste while the 300L fermentation resulted in 4.5 kg cell paste. The final plasmid stability for the GMP fermentation was 36%. Although the use of Origami (DE3) increased the proportion of r-AMA1/E in the soluble fraction (compared to the conventional BL21 (DE3) strain), protein fractionation experiments showed that a majority of r-AMA1/E was still localized in the insoluble fraction (data not shown).

EXAMPLE 2

Figure 2A:
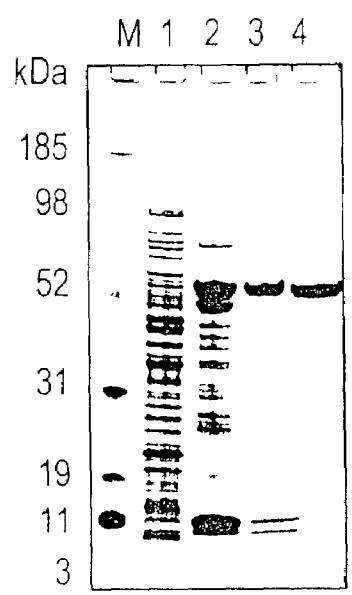
FIG. 2A and 2B. 2A. SDS-PAGE analysis of AMA1/E during purification: Results from a lab-grade purification starting with 20 g of cell paste. Protein analysis was done on a 4–12% gradient gel under reduced conditions and the gel was stained with Coomassie blue. The elutions off DEAE and SP Sepharose columns were concentrated on a 3.5 K cut-off Centricon concentrator before loading. Lane 1, *E. coli* lysate loaded on the $Ni^{+2}$ column; lane 2, $Ni^{+2}$ column elution; lane 3, DEAE Sepharose column elution (5 μg protein); lane 4, SP Sepharose column elution (5 μg protein; lab-grade AMA1/E product). 2B. Western blot analysis for *E. coli* protein detection (Cygnus HCP detection kit). Lanes 1–5, Origami (DE3) bacterial lysate with 4000, 2000, 1000, 500 and 250 ng protein respectively; lanes 6–11, AMA-1/E product at 1, 10, 100, 500, 1000 and 2000 ng protein per well, respectively.

Extraction of r-AMA1/E in sarkosyl and its enrichment by Ni$^{+2}$ affinity chromatography: Aliquots were taken from the GMP cell paste lot and a scalable refolding and purification process was developed. During cell lysis soluble and insoluble forms of r-AMA1/E were extracted with buffer containing 5% sarkosyl. The r-AMA1/E constituted ~1–2% of total cell protein estimated by laser densitometry of a SDS-PAGE run under reduced conditions (FIG. 2A, lane 1). Following the first step of purification over Ni$^{+2}$ column, r-AMA1/E was enriched to ~40 % of total protein (FIG. 2A, lane 2). A large fraction of r-AMA1/E present in the Ni$^{+2}$ elution, was aggregated as seen on a non-reduced SDS-PAGE (data not shown).

EXAMPLE 3

Optimization of the refolding conditions: In order to find the optimal refolding conditions, the Ni$^{+2}$elution was subjected to rapid dilution in refolding buffers of varying GSH/GSSG ratios, at pH 8.0, in phosphate buffer. Serial dilutions of these test refolding mixtures were coated on a microtiter plate and ELISA reactivity against the conformation specific, inhibitory, monoclonal antibody 4G2dc1, was used as a measure of folding efficiency; while the reactivity to a monoclonal anti-hexa-histidine antibody was used to confirm equivalent coating efficiency. Ratios of GSH/GSSG tested for refolding included 1/0.1 mM, 1/0.25 mM, 1/1 mM, and 0.1/1 mM respectively, while phosphate buffer containing EDTA (pH 8.0) alone was used as a control. The GSH/GSSG ratios of 1/0.1 mM and 1/0.25 mM were found to be equally efficient, both of which gave 4G2dc1 reactivity about 5 times higher than the phosphate buffer control. As the GSH/GSSG ratio of 1/0.25 mM had been previously reported for efficient refolding of *P. chabaudi* AMA1and more recently, the same was used to refold *P. falciparum* AMA1expressed in *E. coli* (Crewther et al., 1996, Infect. Immun. 64, 3310–3317; Hodder et al., 2001, supra), we chose this ratio to refold r-AMA1/E. After refolding r-AMA1/E was designated as AMA1/E. A minimum 40-fold dilution of the Ni$^{+2}$ elution to about 20 µg ml$^{-1}$ protein during refolding, was found necessary to minimize aggregation. No significant increase in monomer yield of AMA1/E was found if the Ni$^{+2}$ elution was first reduced with DTT prior to refolding, and therefore, the GMP purification process was carried out using the Ni$^{+2}$ elution without reduction. The presence of low concentrations of sarkosyl (0.003%) in the refolding mix eliminated the need for a cosolvent during refolding.

EXAMPLE 4

Ion-exchange chromatography was used to purify AMA1/E to homogeneity: After 15 h incubation in the refolding buffer, AMA1/E was concentrated on a DEAE anion-exchange column and its monomeric form was eluted with 100 mM NaCl, while the impurities and AMA1/E aggregates remained bound to the column. The percent purity of AMA1/E after this step was ~90 % of the total protein eluted (FIG. 2A, lane 3). The pH adjustment step from pH 8.0 to 5.7 was needed to bind the majority of AMA1/E to the SP cation-exchange column. This pH change had no effect on the solubility of AMA1/E or its reactivity to immune reagents. AMA1/E bound to the cation-exchanger was eluted with the final formulation buffer, eliminating the need for an additional buffer exchange step before formulation. The final yield of AMA1/E was about 0.75 to 1 mg L$^{-1}$ culture with >99% purity estimated by laser densitometry of Coomassie blue stained gels (FIG. 2A, lane 4). RR-AMA1/E also gave similar yield and purity (data not shown).

EXAMPLE 5

Lyophilized formulation of AMA1/E along with sucrose and EDTA was stable: A final 3.15% sucrose excipient was added for stabilization and cake formation during lyophilization. AMA1/E, vialed at 100 µg ml$^{-1}$ in 0.65 ml aliquots, was found to be stable in its lyophilized form at 37° C., 22° C. and 4° C. over a 24 wk period, with no signs of breakdown or aggregation. Solution or lyophilized forms of AMA1/E stored at −30° C. or −70° C. showed equivalent stability (data not shown).

EXAMPLE 6

Figure 2B:
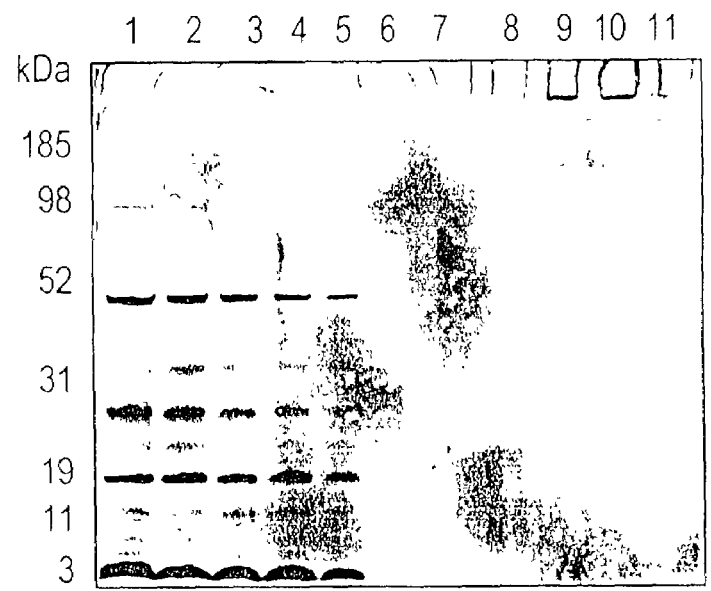

Formulated AMA1/E product has very low residual endotoxin, host cell proteins or sarkosyl content: The endotoxin content of purified AMA1/E under lab conditions was between 3 to 5 EU's per 50 µg protein but dropped to below 0.06 EU (lowest value detectable by LAL assay) per 50 µg protein in GMP purification. No residual sarkosyl was detected with an RP-HPLC based assay (minimum detection limit 0.0005%). The HCP content was determined by ELISA, using an anti-*E. coli* antibody kit, capable of quantitatively detecting 15 ng ml$^{-1}$ HCP using the Origami (DE3) *E. coli* lysate (the lowest concentration of HCP tested). AMA1/E sample at 10,000 ng ml$^-$showed 54 and 44 ng ml$^{-1}$ HCP (in two tests), giving the final purity of 99.4%. Purity of AMA1/E was also tested by western blot HCP determination kit (Cygnus). The Origami (DE3) lysate was used as positive control at 4000 to 250 ng protein per well (FIG. 2B). All the positive bands at 4000 ng per well (FIG. 2B, lane 1) were also observed at 1000 ng per well (FIG. 2B, lane 3). Below 1000 ng per well, many *E. coli* protein bands were not detectable. No *E. coli* specific bands were seen in AMA1/E lanes with up to 2 µg AMA1/E loaded per well (FIG. 2B, lane 11).

EXAMPLE 7

Figure 3A:
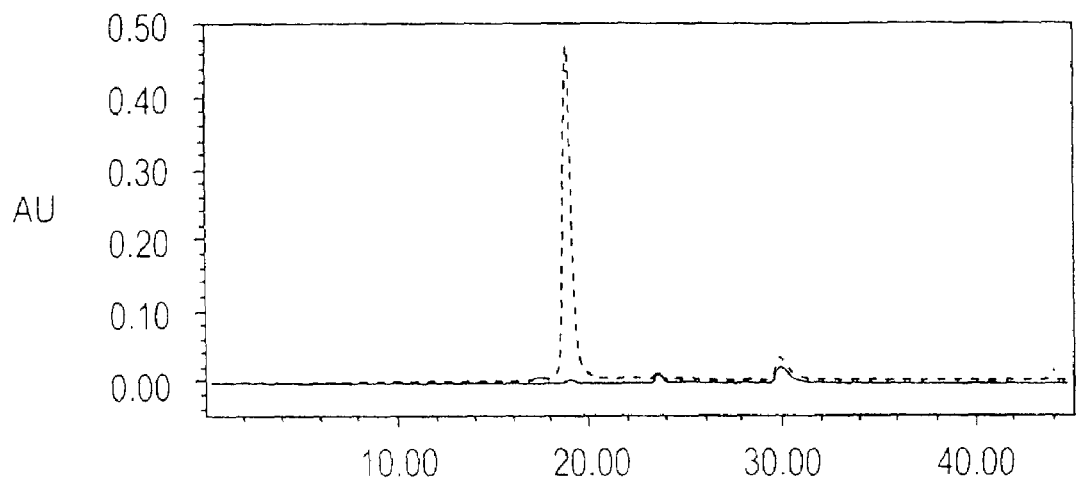
FIG. 3A and 3B. Analytical HPLC profile of the AMA1/E product: Detector output at 215 nm with absorbance units (AU) plotted against time (min). (A) Gel-permeation Shodex Protein KW-803 column elution profile with 10 μg AMA1/E injected (broken line); equal volume of final formulation buffer with no protein injected (solid line). (B) Reversed-phase C8 Aquapore RP-300 Å, 7μ, 30×2.1 mm column elution profile, with 4 μg AMA1/E injection (solid line); shift in retention time observed under the same chromatographic conditions with 12 μg AMA1/E reduced in the presence of 6M guanidine HCl and 25 mM DTT and injected (broken line). See Materials and Methods for solvent and gradient information.
Figure 3B:
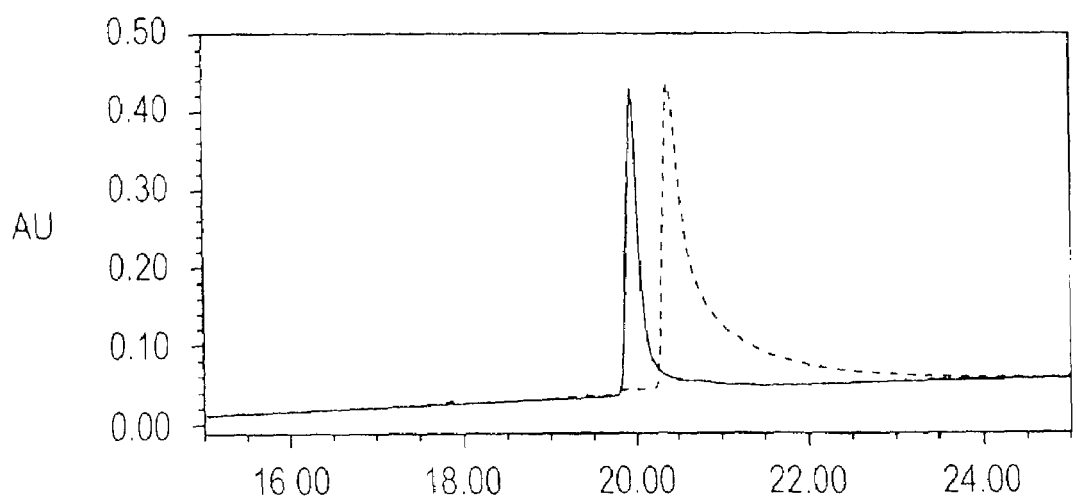

AMA1/E had the predicted primary and tertiary structure with no free cysteines: The primary sequence analysis of AMA1/E identified the first 24 N-terminal amino acids to be ahhhhhhpggsgsgtmhGAEPAP (SEQ ID NO: 5) (*P. falciparum* AMA1 specific residues in capital). The methionine at the N-terminal could not be identified. The MALDI-TOF mass spectrometer analysis showed an average mass at 54,656 Da, while the predicted mass of AMA1/E was 54,633 Da. The final product was evaluated for homogeneity and the presence of multimers by analytical RPC and GPC. A single peak was seen on both GPC and RPC elution profiles, giving evidence of a homogenous product (FIG. 3A, B). The RPC elution profile of AMA1/E, shifted towards higher hydrophobicity under reducing condition (FIG. 3B, broken line). This indicates exposure of the protein hydrophobic core, upon DTT reduction, which otherwise, remained buried due to compact folded state, stabilized by disulphide bond formation.

Figure 4A:
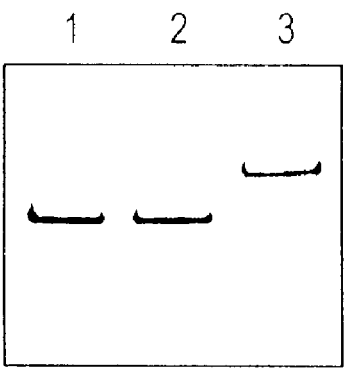
FIG. 4A, 4B, and 4C. Relative SDS-PAGE mobility, alkylation analysis and immune reactivity of AMA1/E: Lane 1, AMA1/E protein (~200 ng) in 4 M urea; lane 2, AMA1/E in 4 M urea treated with iodoacetamide; lane 3, AMA1/E in 4 M urea, reduced with DTT followed by iodoacetamide treatment (see Materials and Methods for reaction details). (A) Proteins separated on a non-reducing 4–12% gradient gel and stained with Coomassie blue. (B) Western blot of the gel shown in (A), immuno-stained with mAb 4G2dc1 and developed with HRP-POD substrate. (C) Western blot of the gel shown in (A), immuno-stained with an immune serum pool collected from Western Kenya and developed with HRP-POD substrate.

The primary structure of AMA1/E is expected to contain 16 cysteine residues, the presence of any free cysteines in the final product, which would have indicated incorrect folding. The free cysteine content was determined by Ellman's test. Ellman's analysis was also carried out in the presence of 4M GuHCl to unmask any sulfhydryl groups buried in the hydrophobic core of the protein. Ellman's test detected no free sulfhydryl groups in up to 5 µM AMA1/E, both in the presence and absence of 4M GuHCl (minimum detection limit 0.1 µM free sulfhydryl). The absence of free cysteines was further confirmed by treating AMA1/E with an alkylating agent before and after reduction. Mobility of AMA1/E on non-reduced SDS-PAGE showed no observable change after treatment with iodoacetamide (FIG. 4A, lanes 1 and 2), while its reductive-alkylation caused significant decrease in mobility (FIG. 4A, lane 3). A recombinant *P. vivax* MSP-1 p42 fragment (Dutta et al., 2001, Infect. Immun. 69, 5464–5470), which was predicted to contain a single free cysteine, was used as a positive control in both the Ellman's and alkylation analysis and this free cysteine was identified in both tests (data not shown). The above tertiary structure analysis also suggests that, as in the case of *P. chabaudi* AMA1(Hodder et al., 1996, supra), the majority of AMA1/E molecules also had all 16 cysteines cross-linked by disulphide bonds.

EXAMPLE 8

Figure 4B:
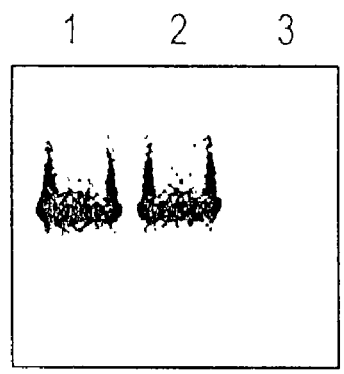
Figure 4C:
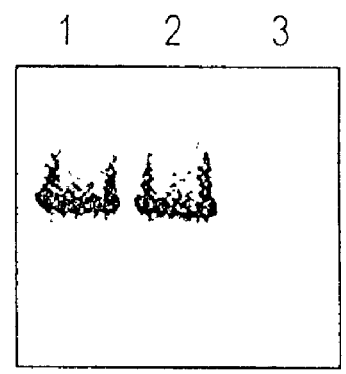

AMA1/E reacts with conformation dependent immune reagents: AMA1/E reacted with the monoclonal antibody 4G2dc1 on immunoblot (FIG. 4B, lane 1). This monoclonal antibody recognizes a reduction sensitive epitope on AMA1of *P. falciparum* (Kocken et al., 1998 supra). Reactivity on immunoblot was also observed with a hyperimmune malaria endemic serum pool from Kenya (FIG. 4C, lane 1). Alkylation of AMA1/E caused no change in its reactivity to the above two immune reagents (FIG. 4B, lane 2 and 3C, lane 2). However, significant loss of reactivity to both immune reagents was observed upon reductive-alkylation (FIG. 4B, lane 3 and 3C, lane 3), further confirming the presence of critical reduction sensitive epitopes on AMA1/E.

EXAMPLE 9

AMA1/E was found to be immunogenic in rabbits: Immunization of rabbits, with lab-grade AMA1/E and RR-AMA1/E at 100 µg per dose was done to determine if one form was immunologically superior to the other. A group of 3 rabbits was immunized with 100 µg per dose RA-AMA1/E to determine if disulphide bond independent epitopes also contributed towards the induction of inhibitory anti-AMA1antibodies. The AMA1/E protein produced under GMP conditions was immunized at 50 and 100 µg per dose to determine the immunogenicity at the two doses (50 µg is the expected human dose). No apparent signs of toxicity of the antigen-adjuvant combination was observed in the immunized animals. Table 1 shows the mean log ELISA titer of immunized groups with either AMA1/E or RA-AMA1/E coated on plates. Rabbits in the lab-grade AMA1/E group (R-1, 2, 3) showed high titer antibodies against AMA1/E protein. No significant difference in the titer was observed between 50 and 100 µg GMP protein immunized groups (data not shown), hence all six rabbits are represented by a single group in Table 1. The AMA1/E specific titers observed in the 50 and 100 µg GMP produced AMA1/E group (V-2, 3, 4, 9, 10, 11) were higher than the 100 µg lab-grade AMA1/E group (2 tailed t test, p=2.5E-04), The RR-AMA1/E group (R-4, 5, 6) also had high ELISA titer against AMA1/E coated wells. The mean titer in the RR-AMA1/E group was slightly lower than the lab-grade AMA1/E protein immunized group although the difference was not statistically significant (p=8.2E-01). The ELISA titers against the RA-AMA1/E protein coated wells for lab-grade, GMP produced AMA1/E and RR-AMA1/E groups were lower as compared to the refolded AMA1/E coated wells (p=2.5E-02, 1.2E-04 and 1.8E-02 respectively). One of the 3 rabbits (R-8) immunized with RA-AMA1/E died while handling. Although, the two remaining RA-AMA1/E immunized rabbits (R-7, 10) had high titer of antibody against RA-AMA1/E coated wells, the titer was lower against the refolded AMA1/E coated wells. This difference was not statistically significant (p=3.8E-01).

TABLE 1

| Immunization | Number of animals per group | Mean Log ELISA titer AMA1/E coated | Mean Log ELISA titer RA-AMA1/E coated | N | Mean Log IFA titer Positive Schizonts | N | Mean GIA data percent inhibition | N |
|---|---|---|---|---|---|---|---|---|
| Lab-grade AMA1/E, 100 ug | 3 | 5.60 (0.04) | 4.94 (0.20) | 3 | 4.41 (0.35) | 2 | 57 (17) 68 (11)* | 3 3* |
| GMP AMA1/E, 50 & 100 ug | 6 | 6.01 (0.13) | 5.29 (0.22) | 3 | 4.71 (0.25) | 1 | 84 (4) | 2 |
| RR-AMA1/E 100 ug | 3 | 5.57 (0.19) | 5.01 (0.17) | 3 | 4.06 (0.35) | 2 | 29 (22) 41 (25)* | 2 2* |
| RA-AMA1/E 100 ug | 2 | 4.83 (0.15) | 5.01 (0.17) | 3 | 2.43 (0.11) | 2 | 5 (1) | 1 |
| Adjuvant | 3 | 0.00 | 0.00 | 2 | 0.00 | 1 | −2 (2) | 2 |

Antibody responses and percent inhibition in GIA in vitro with rabbit sera: Log of mean ELISA titers of lab-grade, GMP produced AMA1/E, RR-AMA1/E or RA-AMA1/E groups tested against either AMA1/E or RA-AMA1/E coated on wells. Antibody titers were calculated for an OD = 0.5 using regression analysis on titration curves. Log IFA titer of groups tested on methanol fixed *P. falciparum* (3D7) schizonts. The percent-inhibition of parasite growth, in a 1-cycle assay, under suspension conditions, at 1:5 serum dilution are shown. Percentage inhibition was calculated from the mean parasitaemia of triplicate test and control wells as 100%−((test/control) × 100). Inhibitions in GIA were relative to adjuvant control sera or culture media alone. Initial parasitemias were 0.2% and the final control parasitemias ranged from 2.2% to 3.6%. Compared with growth in media alone (100%), there were no significant differences in the final parasitemia of 12 pre-immune sera (mean ± SD = 97%, ±4% suspension, 102% ± 1% static) or 3 adjuvant only sera (99% ± 3% suspension, 106% ± 2% static).
*values under static GIA conditions. N stands for number of times the experiment was repeated. Number in the brackets represents the SD.

Figure 5A:
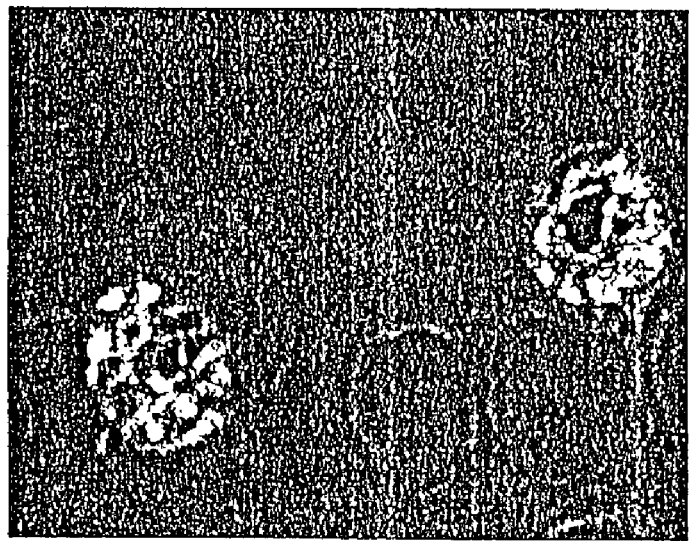
FIG. 5A and 5B. Recognition of the parasite AMA1 with anti-AMA1/E antibodies produced in rabbit: (A) Anti-AMA1/E antibodies (R-1) used for IFA on *P. falciparum* (3D7) parasites fixed with methanol. Merozoites contained within the late-stage schizonts are shown with bright fluorescence (1000X). (B) Western blot of *P. falciparum* 3D7 parasite, late schizont proteins, extracted with SDS-PAGE loading buffer, separated on a non-reducing gel, western blotted and immuno-stained with anti-AMA1/E antibodies and developed with a chemiluminescent substrate. The top and bottom arrows represent ~76 and 62 kDa respectively. Lane 1, post-immune rabbit sera (R-1); lane 2, pre-immune serum control.

Sera from all AMA1/E immunized rabbits tested positive by IFA with late stage schizonts of 3D7 parasites (FIG. 5A). Table 1 shows the mean log IFA titer of the groups. The IFA titer in the GMP produced AMA1/E group was higher than the lab-grade AMA1/E group, although the difference was not significant (p=2.7E-01). The lab-grade AMA1/E group had slightly higher IFA titers than the RR-AMA1/E group, this difference was also not significant (p=2.8E-01). The IFA titer of lab-grade, GMP produced AMA1/E and the RR-AMA1/E groups, were significantly higher than the RA-AMA1/E group titers (p=5.4E-03, 1.5E-05 and 8.6E-03 respectively).

Figure 5B:
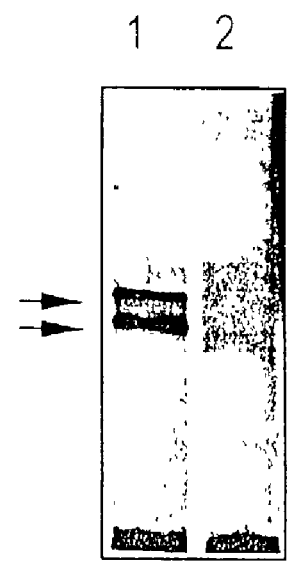

Rabbit antibodies reacted with two bands one ~76 kDa and another at ~62 kDa on western blot of an SDS extract of schizont rich preparation of *P. falciparum* 3D7 parasites (FIG. 5B, lane1). These bands most likely correspond to the previously reported 83 and 66 kDa full length and processed forms of AMA1 in *P. falciparum* (Narum and Thomas, 1994, supra; Howell et al., 2001, supra); difference in apparent molecular weights observed here may be a result of difference in PAGE conditions.

EXAMPLE 10

Anti-AMA1/E antibodies inhibit in vitro growth of the parasite: The growth inhibition assay (GIA) of homologous 3D7 *P. falciparum* parasites was carried out with sera obtained from the immunized rabbits. Table 1 shows the mean percent inhibition, under suspension conditions, at 1:5 dilution obtained for each of the immunized groups. The lab-grade and GMP produced AMA1/E group sera showed significant inhibition of parasite growth, compared to the adjuvant controls (p=2.4E-02, 1.1E-09 respectively). The lab-grade AMA1/E group sera analyzed under static GIA conditions, gave even higher inhibition compared to the suspension culture, although the difference between static and suspension culture values was not significant (p=8.4E-02) (Table 1). Rabbits immunized with 50 and 100 μg doses showed no significant difference in the percent inhibition (data not shown). The RR-AMA1/E immunized group sera showed lower level of inhibition when compared lab-grade AMA1/E group, both under suspension (p value=1.5E-01) and static conditions, (p=1.9E-02); the difference was not statistically significant under suspension conditions. There was a positive correlation between log ELISA and log IFA titers ($R^2$=0.84). There was also a positive correlation between log ELISA against the AMA1/E protein coated wells and the percent GIA ($R^2$=0.81). A positive correlation was also observed between the log IFA titer and percent inhibition ($R^2$=0.77). The above $R^2$ values were calculated using data from all the immunized rabbits in all the groups. No inhibition was seen in RA-AMA1/E group compared to the lab-grade AMA1/E group (p=3.1E-02). In comparison to the growth in media alone (100%) there were no significant differences in the final parasitaemia of 12 pre-immune sera (mean±SD=97±4%) or the 3 adjuvant alone sera (99±3%). Whole serum from one of the rabbits (R-3), which showed 44% inhibition in the one cycle suspension GIA, was used in a two-cycle suspension GIA at the same dilution. Inhibition of 87% was seen, indicative of cumulative inhibition over two cycles.

Figure 6:
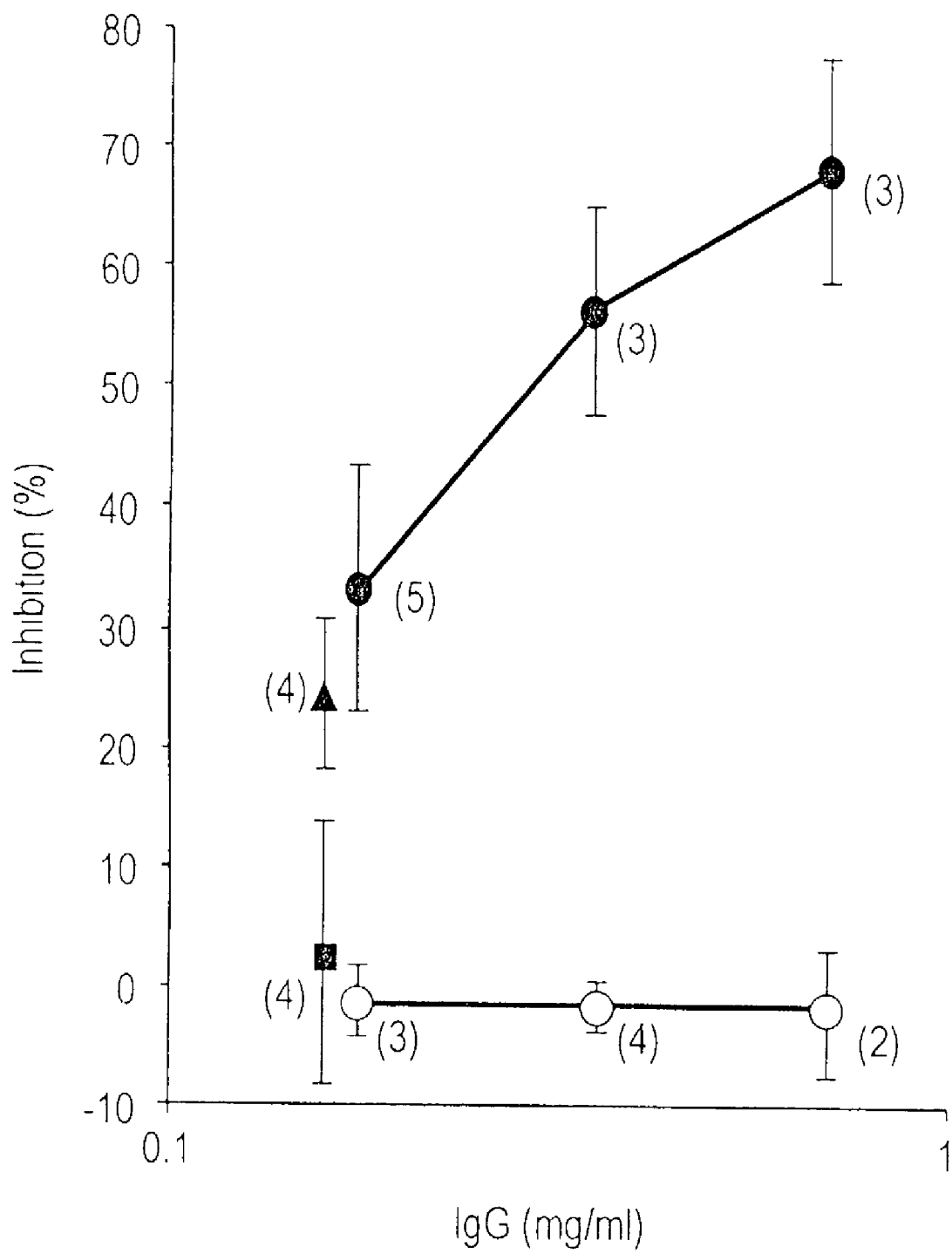
FIG. 6. Purified anti-AMA1/E IgG inhibited growth by *P. falciparum* 3D7 parasite in a GIA and the inhibition was reversed by addition of the antigen. One-cycle GIA with 0.18, 0.35, or 0.7 mg ml$^{-1}$ purified rabbit IgG in suspension culture GIA in 48-well plates. Solid circle=anti-AMA1/E IgG; open circle=anti-RA-AMA1/E IgG. Antigen (5.3 µg ml$^{-1}$) added to 0.18 mg ml$^{-1}$ anti-AMA1/E IgG; solid triangle=RA-AMA1/E antigen added; solid square=AMA1/E antigen added (symbols are offset for clarity). Mean±SD shown along with number of experiments for each data point are represented within brackets.
Figure 7:
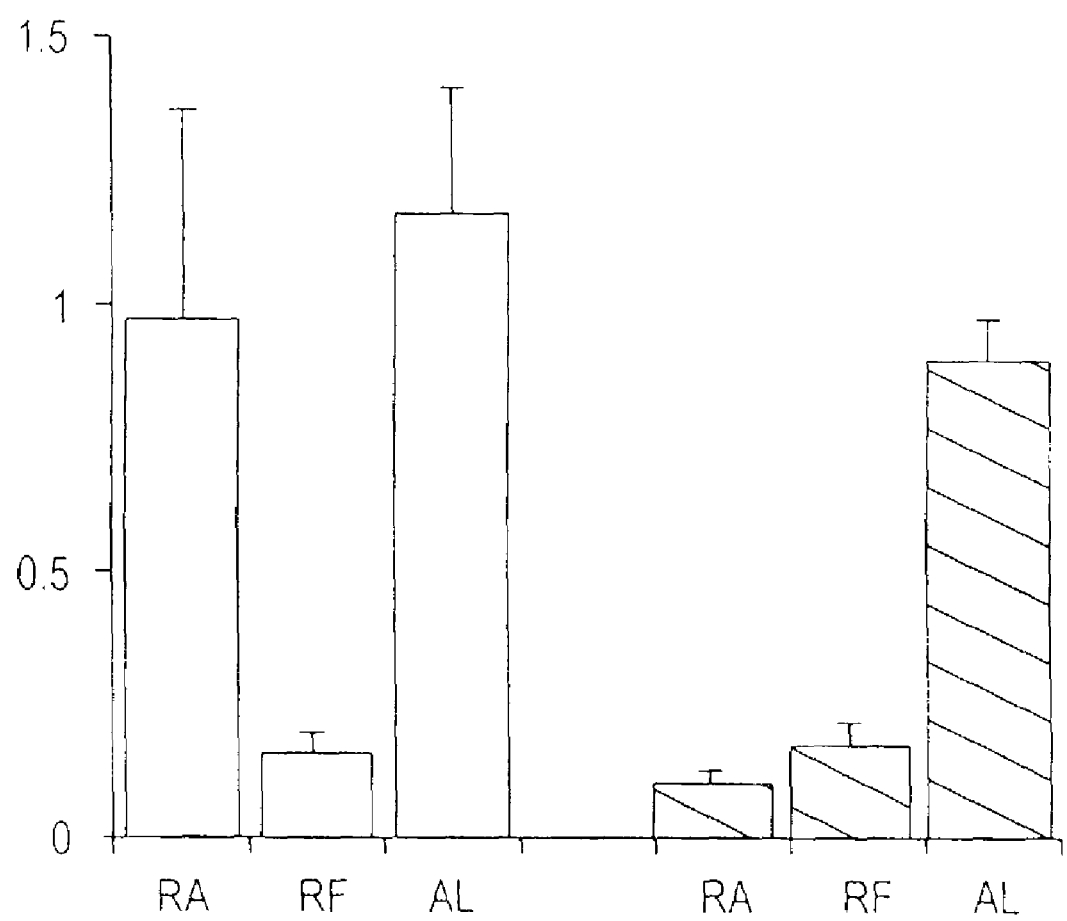
FIG. 7. Competitive ELISA using individual sera. Sera samples at 1:1000 dilution were pre-incubated with either RA-AMA1/E (RA), AMA1/E (RF) or with bovine serum albumin protein (AL). ELISA was done to assay for anti-AMA1/E specific antibodies. Shown here is the average $OD_{405}$ at 1:16000 dilution for AMA1/E immunized rabbits (R-1, 2 and 3), represented by clear bars. RA-AMA1/E immunized rabbits (R-7 and 10), represented by black bars. Mean+SD is represented by a line on top of each bar.

Inhibition of parasite growth was also observed with IgG purified from pooled sera of the rabbits within the lab-grade AMA1/E, RA-AMA1/E and the adjuvant control (FIG. 6). The percent inhibition in the AMA1/E group was significantly higher than the adjuvant control at 0.18, 0.35 and 0.7 mg ml$^{-1}$ IgG concentrations tested (p=7E-04, 8E-03 and 6E-03 respectively). No inhibition was observed with the RA-AMA1/E group IgG was compared to the equivalent IgG concentration from the adjuvant control. In order to determine if the inhibition caused by the IgG could be reversed, identical concentration of AMA1/E or RA-AMA1/E proteins were added to the culture during the GIA. The addition of 5.3 μg ml$^{-1}$ AMA1/E protein to the 0.18 mg ml$^{-1}$ anti-AMA1/E IgG significantly reverses inhibition compared to the addition of the same amount of RA-AMA1/E (p=6E-03) (FIG. 6). This data indicates the critical role of disulphide bonds in the formation of epitopes that can induce inhibitory anti-AMA-1 antibodies.

ELISA, IFA and GIA data with antibodies to recombinant AMA1/E, suggested that the conformational epitopes present on the refolded protein (in addition to the linear epitopes) were indeed highly immunogenic. A competition ELISA using sera from three rabbits in the lab-scale AMA1/E group (R-1, 2, 3) and two rabbits in the RA-AMA1/E group (R-7, 10) was done by pre-incubation with the 15 µg ml$^{-1}$ of AMA1/E, RA-AMA1/E or with BSA as control. FIG. 6, shows the mean $OD_{405}$ at 1:16,000 serum dilution for the two groups along with the SD for 3 experiments. Pre-incubation with the refolded AMA1/E protein resulted on average 86% and 81% reduction in $OD_{405}$ in AMA1/E and RA-AMA1/E groups respectively, in comparison to the BSA control values in the same group (p=1.99E-13 and 1.55E-10 respectively). Although, RA-AMA1/E protein pre-incubation resulted in an average 89% drop in the $OD_{405}$ in the RA-AMA1/E immunized group (p=5.63E-09), it resulted in an insignificant, 16% drop in the refolded AMA1/E group (p=0.071). This data further suggests that a large proportion of the antibodies against refolded AMA1/E were against disulphide bond dependent epitopes.

EXAMPLE 11

Monkey trials. We assessed the safety and immunogenicity of AMA-1/E in rhesus monkeys. The formulation of AMA-1/E was tested in combination with each of four different adjuvants (AS02A, AS02V, AS01B and AS03) in groups of 7 rhesus monkeys at the proposed human dose (50 µg) for safety and immunogenicity. A saline control group of 4 monkeys was included to control for the stress of the numerous animal manipulations. The objective of this study was to determine whether the AMA-1/E antigen with this panel of adjuvants was safe and immunogenic.

Studies were conducted in adult *Macaca mulatta* housed at WRAIR, Forest Glen Annex, Washington D.C. The adult rhesus monkeys used were purpose-bred in the United States from Indian-origin stock. Animals were included if they met all four of the following criteria: in good apparent health on physical exam, baseline hematology or clinical pathology values within the normal range established by our in-house laboratory, negative for known simian retroviruses by serology and PCR, and no prior exposure to malaria or malaria antigens. The monkeys ranged in size from 4.8–13.9 kg, and consisted of both males and females ranging in age from five to twelve years of age. Animals were randomly assigned to treatment groups that were formulated to be as closely matched as possible for sex, age, and body weight, and then the groups were randomly assigned to a treatment protocol. Vaccines were administered in a blinded standardized fashion while animals were under ketamine/acepromazine or ketamine/valium sedation.

Animals received intramuscular injections of AMA-1/E (50 µg) in AS02A adjuvant (clinical lot number 0864, vialed in 0.6-mL aliquots) at 0, 4, and 8 weeks. The veterinarian administering the immunizations and performing the examinations, and all personnel performing laboratory analyses, remained blinded as to which group the monkeys were in until three weeks after the last immunization. All immunization sites were shaved and marked with indelible ink circles to facilitate follow-up examination prior to injection. All immunizations were administered intramuscularly into a single site in the rectus femoris muscle. For safety and reactogenicity data collection, each monkey received a directed examination of spleen, lymph nodes, joints, injection site (using the contralateral site for comparison) and vital signs on the day of immunization (day 0) and at 1, 2, 3, 7, and 14 days after each injection. Blood was obtained for CBC and selected serum chemistries on the same schedule.

EXAMPLE 12

Safety Evaluations:

Physical Evidence of Reactogenicity:

Clinical evaluations before and after each immunization revealed minimal local and no systemic toxicities. Vital signs were taken upon all animal manipulations. As there was quite a bit of variability between individuals, and even within the same individual among different time points, fever was defined as a temperature above two standard deviations of the four-month overall mean of each animal's body temperature. Five fevers were observed in five different animals during the course of the study. None of the fevers exceeded 104.7° F. and none exceeded three standard deviations of the animal's individual mean temperature. Three of the five fevers occurred 24 hours after the first immunization; two in the AMA-1/AS02A group and one in the AMA-1/AS03 group. However, as the other two fevers occurred in the saline control group two weeks after an injection and in the AMA-1/AS03 group one week after injection, it is hypothesized that these represented scattered and transient elevations attributable to the stress of multiple repeated sedation and manipulation. There were no significant alterations in pulse or respiratory rate in any animal.

Spleen size was palpated in every animal at Days 0, 1, 2, 3, 7, and 14 after each injection. Spleens were scored on a ordinal scale of 0, 1, and 2, and 3 where 0 was not palpable or palpably normal, 1 was slightly enlarged or slightly firmer than normal, 2 was moderately enlarged and/or firmer than normal, and 3 was markedly enlarged and firm. There were no scores of 2 or 3 in the entire study. The highest score after each injection for each monkey was corrected for baseline (only needed in one monkey), and tabulated (data not shown). The AS01B and AS03 groups both contained one monkey each that was too fat to clearly evaluate the spleen by palpation; those two individuals did not receive a score. There were no statistical differences between groups.

Both axillary and both inguinal lymph nodes also were palpated on the same schedule as the spleens. The nodes were scored on the following ordinal scale: 0 was a node that was small, soft, and flat; 1 was either larger than normal, firmer and/or more spherical than normal, or more numerous than normal; 2 had two of the above conditions; and 3 had all three. All lymph nodes fluctuated somewhat throughout the study in all monkeys. This data was transformed by looking only at the relationship of the draining inguinal node to the contralateral node for each injection in each monkey. If the two inguinal nodes had been scored the same on the above scale at all time points after the injection, a value of 0 was assigned to that injection. If the draining node was slightly larger, firmer, or more numerous than the contralateral side, a score of 1 was assigned. Finally, if the draining node was markedly different than the contralateral side, a score of 2 was assigned. Each monkey thus contributed three scores, one for each post-injection observation period, to its group. Data indicate that there were no significant differences between any groups (data not shown).

Redness of the overlying skin was also evaluated on an ordinal scale of 0 being normal, 1 being a slight but noticeable diffuse pink flush, and 2 being a marked reddish-pink flush (data not shown). There were significantly more pink flushes in the AMA-1/AS02A group than in any other group except AMA-1/AS02V. The fewest flushes were seen in the AMA-1/AS03 group and in the saline control group.

There were significant differences between groups in the amount of muscle swelling that was detected by palpation after vaccination. Muscle swelling always was evaluated by holding both legs extended and comparing the vaccinated side with the contralateral side. Muscles were scored as not swollen, mildly swollen, moderately swollen, or markedly swollen. The maximum swelling score for the six time points after each injection was determined in order to summarize the data. A score of 0 meant that the muscle was normal at all time points after the injection; a score of 1 was at least one time point after the injection (usually Day 1 and Day 2 post injection) where there was a mild but noticeable swelling of the muscle, and a score of 2 was a muscle that received a moderately swollen rating at some point. No scores of 3, markedly swollen, were recorded in any animal. The data (not shown) indicate that injection of AMA-1 with AS02A resulted in significantly more muscle swelling than with any other adjuvant except AS02V. Co-injection of AMA-1 with AS02V or AS03 gave intermediate amounts of muscle swelling that were different from that seen with plain saline injection. The adjuvant AS01B was the only one that was statistically indistinguishable from the saline controls.

Over the entire study there was only one observation at one time point in one monkey in the AMA-1/AS02A group that the injected muscle felt slightly (1 plus on an ordinal scale of 0–3 plus) warmer in temperature than the contralateral thigh. Injection sites were also palpated for induration, defined as a firm and localized injection site reaction as opposed to a diffuse enlargement of the entire muscle belly. No indurations were ever scored, and there were never any indications of necrosis or any reaction more severe than generalized muscle swelling. At the exact site of needle penetration through the skin, tiny ($\leq$1 mm) red papules were sometimes observed for 1–2 days after injection. These were entirely randomly distributed through groups (data not shown) and thus were interpreted as healing needle marks. There were no incidences of arthritis or any other evidence of systemic effects.

Monkeys were observed for normal behavior twice daily throughout the study. There were no observations of distress, inappetance, or any abnormal behavior. During the weeks of injection, when the monkeys were being sedated once daily, many of them experienced small (<5%) transient losses in weight that were quickly regained over the following weeks.

Hematology:

Blood samples were collected and complete blood count data collected at least every 14 days throughout the study and on Day 0, 1, 2, 3, 7, and 14 of each vaccination.

Mean red blood cell counts (RBCC) by group were compared (data not shown). There were no statistically significant differences between groups at any time. In this study the red cell counts do not reflect either the larger blood collection volumes for cell isolation and cryopreservation just before the start date and at Week 10 or the increased volumes taken immediately after each vaccination. However, there was a transient elevation in mean corpuscular volume (MCV), indicating a response to the blood collections with increased new red cell production, in most of the monkeys at these times (data not shown).

A comparison of the mean white blood cell counts (WBCC) between groups (not shown) indicate that a number of groups demonstrate moderate increases in white cells after each vaccination, most notably the recipients of AMA-1/AS02A, AMA-1/AS02V, and AMA-1/AS01B. None of the group means exceeded the reference range, although in all groups that showed an increase, there were individual values that exceeded that range. In almost all groups there were other apparently random occasional transient individual elevations above reference range that could not be attributed to any particular manipulation or physical finding. In particular, three of the four saline control monkeys experienced a transient WBCC elevation at Week 2 that could not be accounted for by physical exam.

There were no consistent fluctuations in platelet count, and no individual values below the reference range for platelets (210–501/pl) that could not be attributed to very occasional partial clotting of a sample (this occurred less than five times during the study) or to an individual monkey whose counts were always maintained at the low end of normal. There were no other consistent alterations in any of the hemogram parameters.

Clinical Chemistry:

Serum samples were submitted for a small panel of clinical chemistry tests during the pre-bleed period and on Day 0, 1, 2, 3, 7, and 14 of each vaccination. The variables followed were aspartate aminotransferase (AST), alanine aminotransferase (ALT) and gamma-glutamyl transferase (GGT) as measures of hepatic injury, blood urea nitrogen (BUN) and creatinine as measures of renal function, and creatine kinase (CK) an indicator of muscle damage.

Of the three liver-specific enzymes followed, there were consistent transient mild elevations seen in ALT and AST but not GGT after each injection. The mean values for AST (data not shown) slightly exceeded the reference range for this enzyme in all groups. The fact that an identical response was seen in the saline control group provides strong evidence that the observed elevations were an artifact of the stress of multiple sedation and manipulation within the same week, and not a specific effect of either the antigen or the adjuvants. BUN and creatinine were within normal limits in all monkeys prior to the onset of the experiment (data not shown). In all groups, including the saline control group, there was a consistent but not significant decrease in mean BUN values during the week after each injection. The presence of these fluctuations in all groups, including the saline group, enhances confidence that this was an artifact of the repeated sedation and manipulation and was not directly related to the vaccination. No trends or fluctuations were apparent in the creatinine values (data not shown), which remained normal for all monkeys throughout the study.

Vaccination clearly affected the levels of creatine kinase in the serum (data not shown). Even in the saline group, some evidence of muscle damage from injection was indicated by values outside the reference range in all but the last immunization. Although the mean values for the AMA-1/AS02A tended to be the highest, the differences were not statistically different from the other adjuvant groups.

Summary of Safety Data:

All of the tested adjuvants were within acceptable limits in inciting physical evidence of reactogenicity. None of the new adjuvants was any more reactogenic than AS02A, which is already approved for experimental use in humans.

No changes were seen in red cell parameters or in platelet numbers. Changes in the white cell numbers were moderate in all vaccinees, with AMA-1/AS02A giving the greatest magnitude of increase. Coincident with injection, only very small white cell fluctuations were observed in the saline control group. Therefore, all the adjuvants appear to be having some effect on the immune system. However, the magnitude of this effect was relatively small, and was equivalent to unrelated and unexplained fluctuations seen within the saline control group.

Although two of three liver enzymes were consistently elevated after imjection, this appeared to be attributable to the sedatives used and the stress of being handled rather than a direct effect of vaccination, as similar increases were also seen in the saline controls. Kidney function remained normal, in all groups. Damage to muscle was indicated by elevations above reference range values in creatine kinase. All vaccines produced some level of CK elevation. This level of elevation would be considered mild to moderate Therefore, all the tested adjuvants are safe. The new adjuvants had the same or slightly less reactogenicity and similar effects on WBCC and serum chemistry values as AS02A.

EXAMPLE 13

Immunogenicity Results

Generation of anti-AMA-1 antibodies.

The serologic response to immunization with AMA-1 in conjunction with the four tested adjuvants was analyzed by enzyme-linked immunosorbent assay. Briefly, GLP-grade AMA-1 was used to coat the plates at 0.1 µg/well. Sera were serially diluted from 1:50 to 1:6400 and incubated on casein blocked plates for two hours; sera that had titers in excess of 5,000 were rerun at 1:500 to 1:64,000 serial dilutions. Automated platewashers were used throughout, and the peroxidase-conjugated secondary antibody was incubated at 1:2000. Color was developed with ABTS peroxidase substrate. Four-parameter curves were fit to the resultant data and the equation solved for O.D.=1.0 to generate the value that was defined as the titer.

Figure 8:
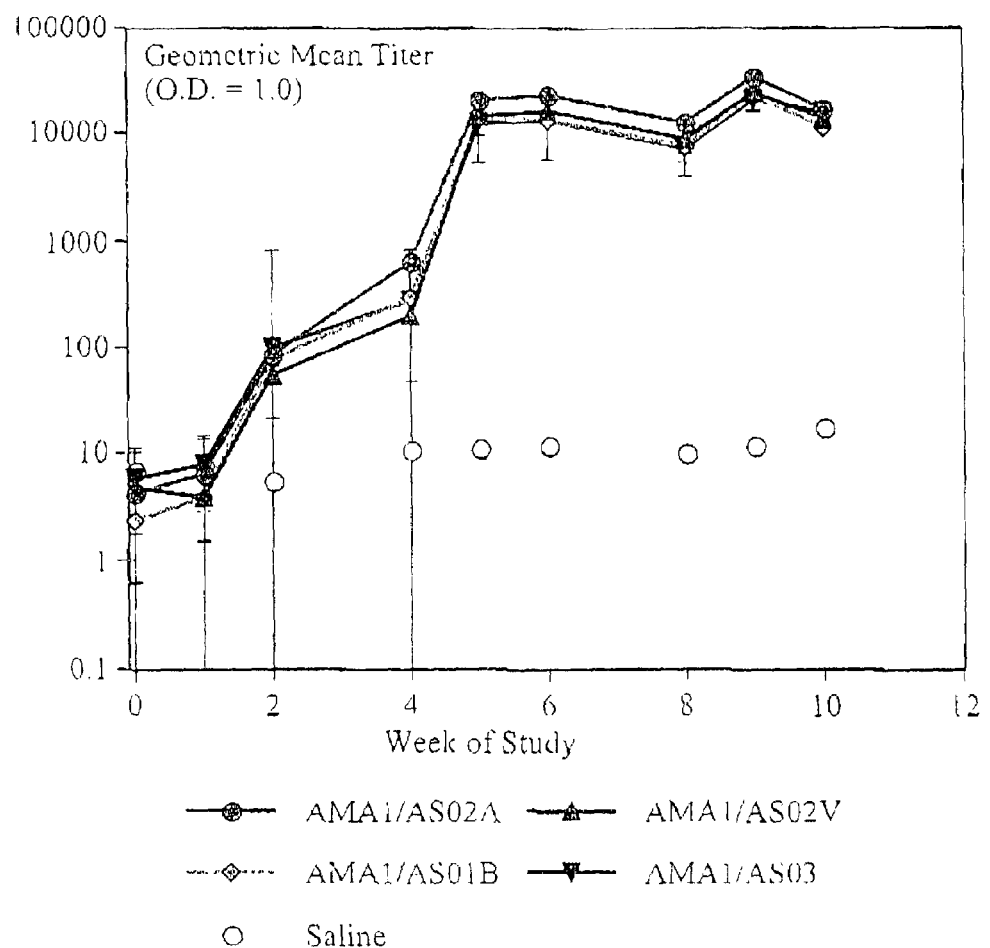
FIG. 8. Geometric mean titer, ±SEM, of anti-AMA-1 antibodies, by group. Titer is defined as the dilution needed to yield an $O.D._{405}$ of 1.0. AMA1/ASO2A, filled circles, AMA1/AS01B (open diamonds), AMA1/AS02V, upright triangles, AMA1/AS03, upside down triangles, and saline, open circles.

The preliminary results are graphed in FIG. 8. AMA-1 was highly immunogenic when administered with any of the tested adjuvants. The geometric mean titer follows almost exactly the same pattern in all groups. Administration of AMA-1 with AS02A gave the highest overall geometric mean titers, and this difference was significant 4 weeks after the first injection when compared with all other groups. AS03 gave the least consistent response after only one vaccination.

One week after the second vaccination all significant differences between groups disappeared. However, the AS03 group continued to have the most variable response, leading to the largest standard error of all the groups. After the third vaccination at Week 8, all monkeys in all groups had mounted responses that gave titers in excess of 7,000. Eight monkeys had titers in excess of 40,000 during the study; four of them were in the AS02A group, and the other three adjuvants had one or two monkeys each with these very high titers. Data on some time points are awaiting re-assay and thus the small differences between groups must still be considered preliminary. However, it is reasonable to conclude that all tested adjuvants can generate geometric mean titers in excess of 10,000.

EXAMPLE 14

Purification of FMP2.1 from *E. coli* Tuner (DE3) cells and testing of FMP2.1 in monkeys.

In order to increase the expression levels of AMA1/E and subsequent purification amounts, the recombinant protein was expressed in *E. coli*, Tuner (DE3) cells. The growth conditions were the same as for *E. coli*, Origami (DE3), as was the purification process. We found that the amount of AMA1/E produced from expression in *E. coli*, Tuner (DE3) (hereafter, FMP2.1) were about 10 times higher than in Origami (DE3) cells. By physical and chemical parameters, including N-terminal amino acid sequencing, mass spectral analysis, HPLC column chromatography for purity, and immuno-reactivity with monoclonal antibodies, the products are identical. In addition, FMP2.1 was shown to induce the same immunological response in mice and rabbits when given identically.

We assessed the safety and immunogenicity of FMP2.1 with the GlaxoSmithKline Biologicals experimental adjuvant AS02A in rhesus macaques. Unpublished data from our laboratories had indicated that rhesus monkeys were much better predictors of immune responses in humans as compared with analogous preclinical studies in mice or rabbits in terms of both humoral and cellular responses to malarial antigens. The formulation of FMP2.1 Lot #0971 was tested in combination with ASO2A adjuvant in a group of 7 rhesus monkeys at the proposed human dose (50 µg) for safety and immunogenicity. A saline control group of 4 monkeys was included to control for the stress of the numerous animal manipulations. The objective of this study was to determine whether the FMP2.1/AS02A formulation was safe and immunogenic when three doses were given one month apart.

Studies were conducted in adult Macaca mulatta housed at WRAIR, Forest Glen Annex, Silver Spring, Md. The adult rhesus monkeys used were purpose-bred in the United States from Indian-origin stock. Animals were included if they met all four of the following criteria: in good apparent health on physical exam, baseline hematology or clinical pathology values within the normal range established by our in-house laboratory, negative for known simian retroviruses by serology and PCR, and no prior exposure to malaria or malaria antigens. The monkeys ranged in size from 5.4–10.1 kg, and consisted of both males and females ranging in age from five to twelve years of age. An associate blinded to treatment group randomly assigned animals to groups that were formulated to be as closely matched as possible for sex, age, and body weight. Vaccines were administered in a blinded standardized fashion while animals were under ketamine/acepromazine or ketamine/valium sedation.

Animals received intramuscular injections of 0.5 ml of FMP2.1 (50 µg) in AS02A adjuvant (clinical lot #0971) at 0, 4, and 8 weeks. The veterinarian administering the immunizations and performing the examinations, and all personnel performing laboratory analyses, remained blinded as to which group the monkeys were in until data collection was finalized three weeks after the last immunization. All immunization sites were shaved and marked with indelible ink circles to facilitate follow-up examination prior to injection. All immunizations were administered intramuscularly into a single site in the rectus femoris muscle of the right thigh. For safety and reactogenicity data collection, each monkey received a directed examination of spleen, lymph nodes, joints, injection site (using the contralateral site for comparison) and vital signs on the day of immunization (day 0) and at 1, 2, 3, 7, and 14 days after each injection. Blood was obtained for CBC and selected serum chemistries on the same schedule.

EXAMPLE 15

Safety evaluations:

Physical Evidence of Reactogenicity:

Clinical evaluations before and after each immunization revealed minimal local and no systemic toxicities. Vital signs were taken upon all animal manipulations. As there was quite a bit of variability between individuals, and even within the same individual among different time points, fever was defined as a temperature above two standard deviations of the four-month overall mean of each animal's body temperature. Using this definition, one fever was observed in one animal at one day after the third injection, but it was only 103.2° F., still considered within the normal range for this species, and still below three standard deviations of the animal's individual mean temperature. One fever also occurred in the saline control group two weeks after an injection. Thus, these may represented scattered and transient elevations attributable to the stress of multiple repeated sedation and manipulation. There were no significant alterations in pulse or respiratory rate in any animal.

Spleen size was palpated in every animal at Days 0, 1, 2, 3, 7, and 14 after each injection. Spleens were scored on a ordinal scale of 0, 1, and 2, and 3 where 0 was not palpable or palpably normal, 1 was slightly enlarged or slightly firmer than normal, 2 was moderately enlarged and/or firmer than normal, and 3 was markedly enlarged and firm. One monkey in the treatment group was too fat to permit accurate evaluation of the spleen by palpation, so data is only available for 6 monkeys. There were no scores of 3 in the entire study, and only one score of 2 in one monkey at one time point. The data over time was collected and analyzed (data not shown). Data indicated that four of six test group monkeys evinced slight splenic enlargement after the second and third injections. The injection group was significantly different from the saline control group.

Both axillary and both inguinal lymph nodes also were palpated on the same schedule as the spleens. Three parameters were palpated for each node locus: volume, firmness or prominence, and number of nodes in the chain. The nodes were scored on the following ordinal scale: 0 for normal, 1 for mild change, 2 for moderate change, and 3 for marked change. All lymph nodes fluctuated somewhat throughout the study in all monkeys, complicating data interpretation. This data was transformed by looking only at the relationship of the draining inguinal node to the contralateral node for each injection in each monkey. If the two inguinal nodes had been scored the same on the above scale at all time points within one week after the injection, a value of 0 was assigned to that injection. If the draining node was slightly larger, firmer, or more numerous than the contralateral side, a score of 1 was assigned. Finally, if the draining node was markedly different than the contralateral side, a score of 2 was assigned. In no case was the draining node found to differ markedly or even moderately from its contralateral mate. However, the percent of nodes that exhibited slight enlargement was statistically higher in the vaccinated group than in the saline group (data not shown).

Redness of the overlying skin was also evaluated on an ordinal scale of 0 being normal, 1 being a slight but noticeable diffuse pink flush, and 2 being a marked reddish-pink flush. Two animals exhibited faint pink flushes on Day 1 after injection in two of their three injections, and one animal in one of three injections. One animal in the saline control group also received a faint pink score after one injection (data not shown).

There were slight statistical differences between groups in the amount of muscle swelling that was detected by palpation after vaccination. Muscle swelling was evaluated by holding both legs extended and comparing the vaccinated side with the contralateral side. Muscles were scored as not swollen (0), swelling barely detectable (1), moderately swollen (2), or markedly swollen (3). No scores of 3, markedly swollen, were recorded in any animal. The data (not shown) indicate that injection of FMP2.1 with AS02A resulted in muscle swelling that was slightly greater than that seen with plain saline injection. Overall, there was a slight statistical difference between groups (p=0.03) that only held up for the first injection when injections were considered individually.

Muscles were also palpated for warmth, comparing right and left sides on the same monkey. No differences were recorded. No indurations of injected material were ever recorded either. At the exact site of needle penetration through the skin, tiny ($\leq 1$ mm) red papules were sometimes observed for 1–2 days after injection. These were entirely randomly distributed across both groups (data not shown) and thus were interpreted as healing needle marks. There were no incidences of arthritis or any other evidence of systemic effects.

Monkeys were observed for normal behavior twice daily throughout the study. There were no observations of distress, inappetance, or any abnormal behavior. During the weeks of injection, when the monkeys were being sedated once daily, many of them experienced small (<5%) transient losses in weight that were quickly regained over the following weeks.

Hematology:

Blood samples were collected and complete blood count data collected at least every 14 days throughout the study and on Day 0, 1, 2, 3, 7, and 14 of each vaccination.

Mean red blood cell counts (RBCC) (data not shown) indicate that there were no statistically significant differences between groups at any time. In this study the red cell counts do not reflect either the larger blood collection volumes for cell isolation and cryopreservation just before the start date and at Week 10 or the increased volumes taken immediately after each vaccination. However, there was a transient elevation in mean corpuscular volume (MCV), indicating a response to the blood collections with increased new red cell production, in most of the monkeys at these times (data not shown).

The mean white blood cell counts (WBCC) (data not shown) indicate mild increase in white cells was seen in some individuals after each vaccination. The increase was only statistically above background after the first injection. The group mean never exceeded the reference range, although occasional individual values transiently did.

There were no consistent fluctuations in platelet count, and no individual values below the reference range for platelets (200–510/µl). There were no other consistent alterations in any of the hemogram parameters except the mild increases in Mean Corpuscular Volume (MCV) noted in some animals after large blood sample collections as a normal regenerative response.

Clinical Chemistry:

Serum samples were submitted for a small panel of clinical chemistry tests during the pre-bleed period and on Day 0, 1, 2, 3, 7, and 14 of each vaccination. The variables followed were aspartate aminotransferase (AST), alanine aminotransferase (ALT) and gamma-glutamyl transferase (GGT) as measures of hepatic injury, blood urea nitrogen (BUN) and creatinine as measures of renal function, and creatine kinase (CK) an indicator of muscle damage.

Of the three liver-specific enzymes followed, there were consistent transient mild elevations seen in ALT and AST but not GGT after each injection (data not shown). The mean values for AST approached or slightly exceeded the reference range for this enzyme. The fact that an identical response was seen in the saline control group provides strong evidence that the observed elevations were an artifact of the stress of multiple sedation and manipulation within the same week, and not a specific effect of either the antigen or the adjuvant. Similar mild transient elevations have been documented in all our other rhesus trials to date.

BUN and creatinine were within normal limits in all monkeys prior to the onset of the experiment. In the test as well as the saline control group, there was a consistent but not significant decrease in mean BUN values during the week after each injection. The presence of these fluctuations in both groups enhances confidence that this was an artifact of the repeated sedation and manipulation and was not directly related to the vaccination. Similar mild transient reductions in BUN have been documented in all our other rhesus trials to date. No trends or fluctuations were apparent in the creatinine values, which remained normal for all monkeys throughout the study (data not shown).

Injection clearly affected the levels of creatine kinase in the serum (data not shown). Even in the saline group, some evidence of muscle damage from injection was indicated by mean values in excess of the reference range in all but the last immunization. The peak mean values for the FMP2.1/AS02A group were about twice as high as for the saline. This is consistent with previous experience with this adjuvant and other antigens tested.

Safety Data Summary:

The tested formulation was within acceptable limits in inciting physical evidence of reactogenicity. This new formulation was no more reactogenic (in fact slightly less, although the comparison was not side-by-side) than RTS,S/AS02A, which is already approved for experimental use in humans.

No changes were seen in red cell parameters or in platelet numbers. Changes in the white cell numbers were modest in all vaccinees. Coincident with injection, only very small white cell fluctuations were observed in the saline control group. Therefore, the formulation does appear to be having some effect on the immune system. However, the magnitude of this effect was relatively small, and was equivalent to or less than fluctuations seen with other formulations with this adjuvant: FMP2.0/AS02A and RTS,S/AS02A (historical data not included).

Although two of three liver enzymes were consistently elevated after injection, this appeared to be attributable to the sedatives used and the stress of being handled rather than a direct effect of vaccination, as similar increases were also seen in the saline controls. Kidney function remained normal in both groups. Mild muscle injury was indicated by elevations above reference range values in creatine kinase in both groups. This level of elevation would be considered mild to moderate.

Therefore, the tested formulation was safe in the rhesus macaque at the target human dosage and administration schedule. This vaccine could be anticipated to cause mild muscle swelling and pain in recipients that is consistent with most other protein antigens in formulation with AS02A.

EXAMPLE 16

Immunogenicity:

The immunogenicity of the construct was determined by enzyme-linked immunosorbent assay (ELISA) using a similarly produced, but not identical, batch of AMA-1 (Lot #0846), i.e. AMA1/E isolated from E. coli, Origami (DE3). Briefly, the plates were coated with AMA1/E at 2 mg/ml, and allowed to incubate overnight. After blocking with 0.5% boiled casein for one hour, the samples are loaded at serial twofold dilutions of 1:50 to 1:6400 or, if titers exceed 5,000, at dilutions of 1:500 to 1:64,000. A two hour incubation is followed by washing and incubation for an hour with peroxidase-conjugated anti-monkey IgG at 1:2,000. The plates are washed again and incubated with ABTS substrate 1:1 with H2O2 for one hour. Plates are read on an automatic plate reader, a fourth order polynomial curve is fitted to the data, and the serum dilution required to yield an optical density of 1.0 is calculated as the titer.

Figure 9:
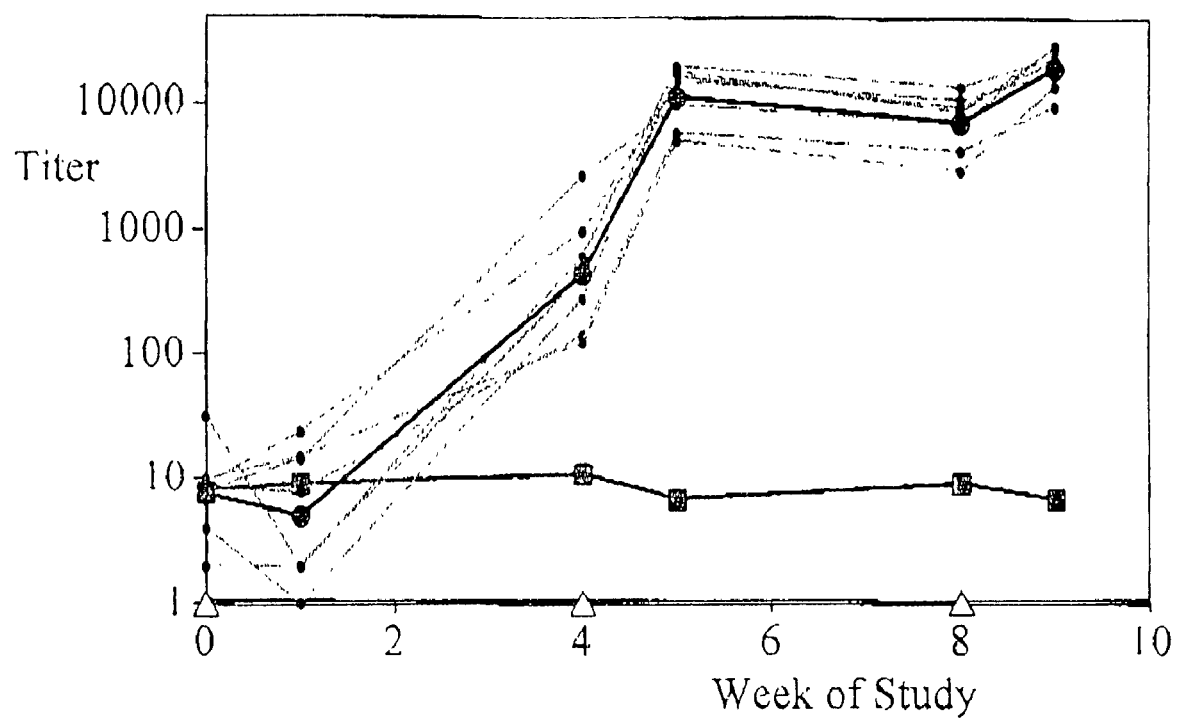
FIG. 9. Anti-AMA1/E ELISA titers over time. Geometric mean titer (circles) and individual monkeys (black dots) in the vaccination group are compared with the mean value in the saline control group (squares). Titer is defined as the serum dilution calculated to give an $O.D._{405}$ of exactly 1.0 in our assay.

The ELISA data is presented in FIG. 9. The first injection of FMP2.1/AS02A instigated an immune response that, by Week 4, had led to a geometric mean titer of about 450. Clearly, the anamnestic response induced by the second immunization immediately boosted the geometric mean titer three fold to about 12,800. The third immunization boosted the geometric mean titer approximately two fold to 30,300. The range of peak titer within the immunized group was 9,900–30,300.

Information from the in vitro parasite growth inhibition assay is still pending. However, clearly this formulation provides excellent immunogenicity against FMP2.1.

DISCUSSION

The availability of a significant quantity of a stable recombinant protein having pharmaceutical levels of purity is an essential step on the path of testing adjuvant combinations capable of inducing a long-lasting and high titer responses in humans. We describe here a process that was successfully scaled-up to produce AMA1/E, a recombinant protein based on the ectodomain of P. falciparum AMA-1. A 300 L fermentation of Tuner strain E. coli cells generated 7.5 kg of cell paste. Starting from 1.0 kg of that paste, 325 mg AMA1/E, was purified. This was enough material to make over 5000 doses of FMP2.1 antigen for immunization. We initially vialed and lyophilized, under a GMP environment, 1500 vials which have undergone and passed all the major criteria set to proceed into a Phase I clinical trial. These include, purity (>99% done by SDS-PAGE and GPC), endotoxin content (0.06 EU per 50 µg protein by LAL test), free thiol content (<0.1 µM free —SH groups per µm protein measured by Ellman's test), positive reactivity to immune reagents (monoclonal antibody 4G2dc1 and malaria immune sera done by western blotting), mass analysis (54,648 Da by MALDI-TOF), correct N-terminal sequence (first 21 residues by Edman's method), host cell protein content (<0.5% by ELISA), western blot (no E. coli specific band with up to 2 µg AMA1/E loaded per well), residual sarkosyl content (below detectable limits by RP-HPLC) and product stability (stable at 37° C. for more than 6 months) in its lyophilized form (data not shown). The GMP produced AMA1/E product, was immunogenic in rabbits and raised high titer inhibitory antibodies.

The correct folding of AMA1, as in case of several other *Plasmodium* antigens, has been shown to be critical for its immunological activity (Anders et al., 1998, supra; Hodder et al., 2001, supra; Crewther et al., 1996, supra). Full length *P. falciparum* AMA1 was first expressed in the eukaryotic insect cell system (Narum et al., 1993, J. Chromatogr. A. 657, 357–363), although the baculovirus product was soluble, the purification strategy was not designed for scale-up production. Prokaryotic expression of AMA1 from various species has been problematic, primarily due to the formation of insoluble aggregates presumably due to incorrect folding of the protein. Previous work on *P. chabaudi* AMA1expression in *E. coli* showed that it was necessary to include an in vitro refolding step in the process in order to obtain correctly folded protein (Anders et al., 1998, supra). A similar approach was successful for obtaining correctly folded AMA1 from *P. falciparum* and the antibodies made against it inhibited parasite growth in vitro (Hodder et al., 2001, supra). A scalable process for the production of recombinant AMA1has not yet been described. Following the success with another malarial antigen (Dutta et al., 2001, supra), we attempted to express r-AMA1/E as a soluble protein in *E. coli*. A 'redox modified' strain of *E. coli*, Origami (DE3), with mutations in the glutathione and thioredoxin reductase pathways (Bessette et al., 1999, Proc. Natl. Acad. Sci. USA 96, 13703–13708) was used for expression, with induction carried out at low temperature and using a minimal IPTG concentration. Despite attempts to optimize the fermentation conditions to obtain soluble r-AMA1/E, a large fraction was still located in the insoluble pellet. Hence, we switched to Tuner (DE3) cells. A downstream purification process was developed to extract r-AMA1/E from both soluble and insoluble fractions and to refold it in vitro.

The increase in reactivity to immune reagents observed after the refolding step and the homogeneity of the final product, justified the need for the inclusion of this refolding step in the process, although, this was a limiting factor during scale up production. A minimum of 40-fold dilution was necessary to gain optimal immune reactivity. An anion-exchange step was used after refolding to separate the monomeric AMA1/E from its aggregated forms, which eluted at a higher NaCl concentration. This monomer selection step resulted in some loss of product during purification. After anion-exchange, a doublet at ~10 kDa, was found to co-elute with AMA1/E and, although GPC was an option, we avoided it due to problems associated with scale-up. Instead, a cation-exchange step using SP-Sepharose was used to purify AMA1/E to homogeneity. Assays based on immuno-detection of HCP's, in combination with laser densitometry of stained polyacrylamide gels and analytical GPC were used to determine that the final product was >99% pure.

N-terminal sequencing and mass spectrometric analysis confirmed the correct primary structure of AMA1/E. Ellman's test and alkylation analysis confirmed the absence of any free cysteines in the final product. Shift in the RPC elution profile under reduced conditions and immunoblot reactivity to a conformation dependent inhibitory rat monoclonal antibody, 4G2dc1, under non-reduced conditions further confirms the disulphide-bonded nature of the antigen.

AMA1/E was found to be highly immunogenic in rabbits in combination with Montanide ISA720 adjuvant. Antibodies raised against the recombinant protein recognized the native parasite AMA1protein both on IFA and western blot. Whole serum from the immunized rabbits showed growth inhibition of the homologous *P. falciparum* (3D7) parasites in vitro both under suspension and static GIA conditions. During this process development, we refolded the r-AMA1/E protein either directly (AMA1/E) or after DTT reduction of the $Ni^{+2}$ column elution (RR-AMA1/E). The RR-AMA1/E product based on its overall lower immunogenicity, lower percent GIA values of its anti-sera, in addition to the observation that DTT reduction gave no significant gain in the monomeric protein yield was not pursued further in the scale-up GMP process.

It has previously been shown that AMA1 based protective immunity can be passively transferred by IgG transfusion into naive animals (Narum et al., 2000, supra; Anders et al., 1998, supra). Antibodies to recombinant AMA1 from *P. falciparum* have recently been reported to inhibit parasite invasion in vitro (Hodder et al., 1996, supra). These data suggest that AMA1based protection is probably antibody mediated. In vitro growth inhibition observed with whole sera and with purified IgG, in addition to the positive correlations observed between the ELISA titer (against AMA1/E coated wells), and IFA titer, suggests that these measures of antibody response might serve as good correlates of AMA1 based protection in vivo. When comparing the same sera in parallel experiments we have observed higher percent GIA values in static culture compared to the suspension GIA (paired t test, p=5E-06). Fluid movement in suspension culture may better mimic the blood flow conditions encountered in vivo by the parasite, than does static culture GIA. Some antibodies are known to show better inhibition in either static or suspension culture (Haynes et al., 2002, supra) and it remains to be seen whether suspension or static culture GIA better predicts protection following vaccination. However, it is encouraging to report that anti-AMA1/E antibodies are inhibitory under both conditions.

Previous data on mice vaccination with recombinant *P. chabaudi* AMA1suggested that, the presence of intact disulphide bonds in the vaccinating AMA1 antigen are necessary to induce protection (Crewther et al., 1996, supra). The data presented here also suggests that disulphide-bond dependent motifs play a critical role in the induction of inhibitory anti-AMA1 antibodies. Higher ELISA titer obtained with refolded AMA1/E coated wells compared to the RA-AMA1/E coated wells in the AMA1/E immunized group, lower IFA titers in the RA-AMA1/E group, inability of the anti-RA-AMA1/E antibodies to block parasite invasion, the ability of AMA1/E and not RA-AMA1/E protein to significantly reverse the in vitro growth inhibition and the ability of AMA1/E and not of RA-AMA1/E, to out-compete binding of most of the anti-AMA1/E antibody to AMA1/E protein on ELISA, indicates that a majority of the immunologically significant epitopes of AMA-1 are sensitive to reduction. In conclusion this application details the process development for the production of a disulfide cross-linked AMA1ectodomain recombinant protein that could serve as a malaria vaccine candidate. Safety, stability and potency tests in animals inidcated that this product is safe to test in humans for its ability to induce a protective immune response to *P. falciparum* malaria.

What is claimed is:

1. An isolated polynucleotide encoding the *P. falciparum* strain 3D7 apical membrane antigen-l (AMA-1) ectodomain protein consisting of amino acids 83–531 of AMA-1.

2. The polynucleotide of claim 1, further comprising a polynucleotide encoding the 6-histidine tag on the carboxy terminal end of the encoded protein.

3. The polynucleotide of claim 2, further comprising a polynucleotide encoding the 6-histidine tag on the amino terminal end of the encoded protein.

4. The polynucleotide of claim 3, said polynucleotide defined in SEQ ID NO: 1.

5. A recombinant vector comprising the polynucleotide of claim 4.

6. The vector of claim 5 wherein said vector is PWR-MAL-AMAI/E.

7. A recombinant vector comprising the polynucleotide of claim 1.

8. A host cell transformed with the vector according to claim 6.

9. The host cell of claim 8 wherein said host is a redox modified host.

10. The host cell of claim 9 wherein said host cell is Origami™ DE3.

11. The host cell of claim 9 wherein said host cell is Tuner™ DE3.

12. A method for isolating and purifying recombinant *P. falciparum* AMA-I protein comprising: growing a host cell containing a recombinant vector expressing *P. falciparum* AMA-1 protein according to claim 7 in a suitable culture medium, causing expression of said vector under suitable conditions for production of soluble AUA-1 protein, lysing said host cells and recovering said AMA-I protein, and refolding said AMA-I protein such that it reacquires its native folding.

13. The method of claim 12 wherein said expression of said vector is by induction with IPTG at a temperature range of 25° C.–30° C.

14. The method of claim 12, wherein said induction is at 28° C.

15. The method of claim 12 wherein lysing of cells is in the presence of a mild detergent.

16. The method of claim 15 wherein said mild detergent is sarkosyl.

17. The method of claim 12 further comprising removal of *E. coli* proteins.

18. The method of claim 17 wherein said removal of *E. coli* proteins is by application to a Ni-NTA column, followed by anion exchange chromatography, followed by cation exchange chromatography.

19. The method of claim 12 wherein said refolding is in the presence of about 1 mM reduced glutathione and about 0.25 mM oxidized glutathione.

20. A method for isolating and purifying recombinant *P. falciparum* AMA-1 protein comprising: growing a host cell containing a recombinant vector expressing *P. falciparum* AMA-1 protein according to claim 6 in a suitable culture medium, causing expression of said vector under suitable conditions for production of soluble AMA-1 protein, lysing said host cells and recovering said AMA-I protein, and refolding said AMA-I protein such that it reacquires its native folding.

* * * * *

SEQUENCE LISTING

<160> NUMBER OF SEQ ID NOS: 5

<210> SEQ ID NO 1
<211> LENGTH: 1437
<212> TYPE: DNA
<213> ORGANISM: Artificial sequence
<220> FEATURE:
<223> OTHER INFORMATION: Expressed partial sequence of Plasmodium falciparum AMA-1

<400> SEQUENCE: 1

```
atggcacacc atcatcatca tcatcccggg ggatccggtt       40
ctggtaccat gcatggggcg gaaccggcgc cgcaggaaca       80
gaacctgttt agcagcattg aaattgtgga acgtagcaac      120
tatatgggca acccgtggac cgaatatatg gcgaaatatg      160
atattgaaga agtgcatggc agcggcattc gtgtggatct      200
gggcgaagat gcggaagtgg cgggcaccca gtatcgtctg      240
ccgagcggca aatgcccggt gtttggcaaa ggcattatta      280
ttgaaaacag caacaccacc tttctgaccc cggtggcgac      320
cggcaaccag tatctgaaag atggcggctt tgcgtttccg      360
ccgaccgaac cgctgatgag cccgatgacc ctggatgaaa      400
tgcgtcattt ttataaagat aacaaatatg tgaaaaacct      440
ggatgaactg accctgtgca gccgtcatgc gggcaacatg      480
attccggata acgataaaaa cagcaactat aaatatccgg      520
cggtgtatga tgataaagat aaaaaatgcc atattctgta      560
tattgcggcg caggaaaaca acggcccgcg ttattgcaac      600
aaagatgaaa gcaaacgtaa cagcatgttt tgctttcgtc      640
cggcgaaaga tattagcttt cagaactata cctatctgag      680
caaaaacgtg gtggataact gggaaaaagt gtgcccgcgt      720
aaaaacctgc agaacgcgaa atttggcctg tgggtggatg      760
gcaactgcga agatattccg catgtgaacg aatttccggc      800
gattgatctg tttgaatgca acaaactggt gtttgaactg      840
agcgcgagcg atcagccgaa acagtatgaa cagcatctga      880
ccgattatga aaaaattaaa gaaggcttta aaaacaaaaa      920
cgcgagcatg attaaaagcg cgtttctgcc gaccggcgcg      960
tttaaagcgg atcgttataa aagccacggc aaaggctata     1000
actggggcaa ctataacacc gaaacccaga aatgcgaaat     1040
ttttaacgtg aaaccgacct gcctgattaa caacagcagc     1080
tatattgcga ccaccgcgct gagccatccg attgaagtgg     1120
aaaacaactt tccgtgcagc ctgtataaag atgaaattat     1160
gaaagaaatt gaacgtgaaa gcaaacgtat taaactgaac     1200
gataacgatg atgaaggcaa caaaaaaatt attgcgccgc     1240
gtatttttat tagcgatgat aaagatagcc tgaaatgccc     1280
```

-continued

| | |
|---|---|
| gtgcgatccg gaaatggtga gcaacagcac ctgccgtttt | 1320 |
| tttgtgtgca aatgcgtgga acgtcgtgcg gaagtgacca | 1360 |
| gcaacaacga agtggtggtg aaagaagaat ataaagatga | 1400 |
| agcggccgca ctcgagcacc accaccacca ccactga | 1437 |

<210> SEQ ID NO 2
<211> LENGTH: 478
<212> TYPE: PRT
<213> ORGANISM: Artificial sequence
<220> FEATURE:
<223> OTHER INFORMATION: Expressed partial sequence of Plasmodium
      falciparum AMA-1

<400> SEQUENCE: 2

Met Ala His His His His His His Pro Gly
                5                   10

Gly Ser Gly Ser Gly Thr Met His Gly Ala
                15                  20

Glu Pro Ala Pro Gln Glu Gln Asn Leu Phe
                25                  30

Ser Ser Ile Glu Ile Val Glu Arg Ser Asn
                35                  40

Tyr Met Gly Asn Pro Trp Thr Glu Tyr Met
                45                  50

Ala Lys Tyr Asp Ile Glu Glu Val His Gly
                55                  60

Ser Gly Ile Arg Val Asp Leu Gly Glu Asp
                65                  70

Ala Glu Val Ala Gly Thr Gln Tyr Arg Leu
                75                  80

Pro Ser Gly Lys Cys Pro Val Phe Gly Lys
                85                  90

Gly Ile Ile Ile Glu Asn Ser Asn Thr Thr
                95                  100

Phe Leu Thr Pro Val Ala Thr Gly Asn Gln
                105                 110

Tyr Leu Lys Asp Gly Gly Phe Ala Phe Pro
                115                 120

Pro Thr Glu Pro Leu Met Ser Pro Met Thr
                125                 130

Leu Asp Glu Met Arg His Phe Tyr Lys Asp
                135                 140

Asn Lys Tyr Val Lys Asn Leu Asp Glu Leu
                145                 150

Thr Leu Cys Ser Arg His Ala Gly Asn Met
                155                 160

Ile Pro Asp Asn Asp Lys Asn Ser Asn Tyr
                165                 170

Lys Tyr Pro Ala Val Tyr Asp Asp Lys Asp
                175                 180

Lys Lys Cys His Ile Leu Tyr Ile Ala Ala
                185                 190

Gln Glu Asn Asn Gly Pro Arg Tyr Cys Asn
                195                 200

-continued

```
Lys Asp Glu Ser Lys Arg Asn Ser Met Phe
            205                 210

Cys Phe Arg Pro Ala Lys Asp Ile Ser Phe
            215                 220

Gln Asn Tyr Thr Tyr Leu Ser Lys Asn Val
            225                 230

Val Asp Asn Trp Glu Lys Val Cys Pro Arg
            235                 240

Lys Asn Leu Gln Asn Ala Lys Phe Gly Leu
            245                 250

Trp Val Asp Gly Asn Cys Glu Asp Ile Pro
            255                 260

His Val Asn Glu Phe Pro Ala Ile Asp Leu
            265                 270

Phe Glu Cys Asn Lys Leu Val Phe Glu Leu
            275                 280

Ser Ala Ser Asp Gln Pro Lys Gln Tyr Glu
            285                 290

Gln His Leu Thr Asp Tyr Glu Lys Ile Lys
            295                 300

Glu Gly Phe Lys Asn Lys Asn Ala Ser Met
            305                 310

Ile Lys Ser Ala Phe Lys Pro Thr Gly Ala
            315                 320

Phe Lys Ala Asp Arg Tyr Lys Ser His Gly
            325                 330

Lys Gly Tyr Asn Trp Gly Asn Tyr Asn Thr
            335                 340

Glu Thr Gln Lys Cys Glu Ile Phe Asn Val
            345                 350

Lys Pro Thr Cys Leu Ile Asn Asn Ser Ser
            355                 360

Tyr Ile Ala Thr Thr Ala Leu Ser His Pro
            365                 370

Ile Glu Val Glu Asn Asn Phe Pro Cys Ser
            375                 380

Leu Tyr Lys Asp Glu Ile Met Lys Glu Ile
            385                 390

Glu Arg Glu Ser Lys Arg Ile Lys Leu Asn
            395                 400

Asp Asn Asp Asp Glu Gly Asn Lys Lys Ile
            405                 410

Ile Ala Pro Arg Ile Phe Ile Ser Asp Asp
            415                 420

Lys Asp Ser Leu Lys Cys Pro Cys Asp Pro
            425                 430

Glu Met Val Ser Asn Ser Thr Cys Arg Phe
            435                 440

Phe Val Cys Lys Cys Val Glu Arg Arg Ala
            445                 450

Glu Val Thr Ser Asn Asn Glu Val Val Val
            455                 460

Lys Glu Glu Tyr Lys Asp Glu Ala Ala Ala
```

```
                        465                  470
Leu Glu His His His His His His
                                    475

<210> SEQ ID NO 3
<211> LENGTH: 18
<212> TYPE: PRT
<213> ORGANISM: Artificial sequence
<220> FEATURE:
<223> OTHER INFORMATION: amino terminus 18 amino acids fused to AMA-1/E

<400> SEQUENCE: 3

Met Ala His His His His His His Pro Gly
                 5                  10

Gly Ser Gly Ser Gly Thr Met His
             15

<210> SEQ ID NO 4
<211> LENGTH: 11
<212> TYPE: PRT
<213> ORGANISM: Artificial sequence
<220> FEATURE:
<223> OTHER INFORMATION: C-terminus 11 amino acids fused to AMA-1/E

<400> SEQUENCE: 4

Ala Ala Ala Leu Glu His His His His His
                 5                  10

His

<210> SEQ ID NO 5
<211> LENGTH: 23
<212> TYPE: PRT
<213> ORGANISM: Artificial sequence
<220> FEATURE:
<223> OTHER INFORMATION: N-terminal 23 amino acids in recombinant
      AMA-1/E

<400> SEQUENCE: 5

Ala His His His His His His Pro Gly Gly
                 5                  10

Ser Gly Ser Gly Thr Met His Gly Ala Glu
             15                  20

Pro Ala Pro
```